(12) United States Patent
Xue

(10) Patent No.: US 11,634,774 B2
(45) Date of Patent: Apr. 25, 2023

(54) GENOME-WIDE CAPTURE OF INTER-TRANSPOSABLE ELEMENT SEGMENTS FOR GENOMIC SEQUENCE ANALYSIS OF HUMAN DNA SAMPLES WITH MICROBIAL CONTAMINATION

(71) Applicant: PharmacoGenetics Limited, Shatin (CN)

(72) Inventor: Hong Xue, Hong Kong (CN)

(73) Assignee: PharmacoGenetics Limited, Shatin (HK)

( * ) Notice: Subject to any disclaimer, the term of this patent is extended or adjusted under 35 U.S.C. 154(b) by 312 days.

(21) Appl. No.: 16/613,667

(22) PCT Filed: May 18, 2018

(86) PCT No.: PCT/IB2018/053534
§ 371 (c)(1),
(2) Date: Nov. 14, 2019

(87) PCT Pub. No.: WO2018/211477
PCT Pub. Date: Nov. 22, 2018

(65) Prior Publication Data
US 2021/0164049 A1    Jun. 3, 2021

Related U.S. Application Data

(60) Provisional application No. 62/507,814, filed on May 18, 2017.

(51) Int. Cl.
*C12Q 1/6883* (2018.01)
*C12Q 1/6827* (2018.01)
*C12Q 1/689* (2018.01)

(52) U.S. Cl.
CPC .......... *C12Q 1/6883* (2013.01); *C12Q 1/689* (2013.01); *C12Q 1/6827* (2013.01); *C12Q 2600/156* (2013.01)

(58) Field of Classification Search
CPC ........................... C12Q 1/6827; C12Q 1/6883
See application file for complete search history.

(56) References Cited

U.S. PATENT DOCUMENTS

2013/0143746 A1 * 6/2013 Xue .................. G16B 20/00
506/2

OTHER PUBLICATIONS

Burns, K.H. and Boeke, J. D. Cell 149:740 (May 11, 2012). (Year: 2012).*
Burns, K. H., et al., "Human Transposon Tectonics," Cell, May 11, 2012, pp. 740-752, vol. 149.

* cited by examiner

*Primary Examiner* — Diana B Johannsen
(74) *Attorney, Agent, or Firm* — Lewis Rice LLC

(57) ABSTRACT

A method for identifying one or more genomic variations in human genomic DNA, comprising employment of Alu, MIR and SVA sequence-based PCR primers and performing an inter-transposable-element (ITE) polymerase chain reaction on the assay mixture to produce an array of amplicons comprising the ITE genomic segments. Also provided the use of the method for identifying one or more genomic variants associated with a trait or a disease.

9 Claims, 12 Drawing Sheets
Specification includes a Sequence Listing.

Distance intervals (in bp) for significant enrichment ($p<0.01$).

| Retrotransposons | SNP1K | MST | shortCNVG | midCNVG | longCNVG | CNVT |
|---|---|---|---|---|---|---|
| SVA_EF | — | — | ≤ 5000 | ≤ 5000 | 3750 - 5000 | — |
| SVA_CD | ≤ 5000 | — | ≤ 5000 | 700 - 5000 | 4250 - 5000 | 4150 - 5000 |
| SVA_AB | ≤ 5000 | — | 600 - 2950 | — | — | — |
| MIR | 1000 - 5000 | 1650 - 5000 | 1400 - 5000 | — | — | ≤ 5000 |
| AluY_young | ≤ 350 | — | ≤ 5000 | ≤ 5000 | 100 - 5000 | — |
| AluY_old | ≤ 3700 | 300 - 750<br>1050 - 2350 | ≤ 5000 | 150 - 5000 | 900 - 5000 | 1500 - 5000 |
| AluS | ≤ 950 | 200 - 5000 | ≤ 5000 | — | 1700 - 5000 | 800 - 5000 |
| Alu_old | — | ≤ 5000 | ≤ 5000 | — | — | 850 - 5000 |

Figure 9

GENOME-WIDE CAPTURE OF INTER-TRANSPOSABLE ELEMENT SEGMENTS FOR GENOMIC SEQUENCE ANALYSIS OF HUMAN DNA SAMPLES WITH MICROBIAL CONTAMINATION

CROSS-REFERENCE TO RELATED APPLICATIONS

This application is a U.S. national stage application of PCT Application No. PCT/IB2018/053534, filed May 18, 2018, which claims the benefit of U.S. Provisional Patent Application Ser. No. 62/507,814, filed May 18, 2017. Each of the above-cited applications is incorporated herein by reference in its entirety.

REFERENCE TO SEQUENCE LISTING SUBMITTED ELECTRONICALLY

The official copy of the sequence listing is submitted electronically via ePCT as an ASCII-formatted sequence listing with a file named "PHGLI002.WO GENE SEQUENCE LISTING", created on May 18, 2018 and having a size of 2.5 kilobytes, and is filed concurrently with the specification. The sequence listing contained in this ASCII-formatted document is part of the specification and is herein incorporated by reference in its entirety.

FIELD OF THE INVENTION

The present invention generally relates to a method for the analysis of sequence and structure variations in human DNA samples contaminated with microbial DNA. More particularly, the invention makes use of the multitudinous insertions of Alu, MIR and SVA retrotransposons in the genome through the amplification of inter-transposable element (ITE) genomic segments using polynucleotide chain reaction (PCR) with Alu-, MIR- and SVA-consensus sequence-based PCR primers, and sequence analysis of the resultant amplicons by means of massively parallel sequencing (MPS) in an 'AlmivaScan' sequencing platform. In keeping with the lack of any known report of Alu, MIR and SVA retrotransposable elements in bacterial and viral DNAs, the present invention finds that genomic analysis of human DNA based on such AlmivaScan sequencing can proceed with minimal interference by the presence of microbial DNAs, which opens up the application of AlmivaScan to the sequence analysis of human DNA in human exudates and excretions that are contaminated with bacteria and viruses.

BACKGROUND OF THE INVENTION

Although human genomic sequences are readily analyzed by a number of methodological platforms including whole genome sequencing ("WGS") and whole exome sequencing (WES), analysis requires the use of human DNA samples uncontaminated by other types of DNA. Accordingly, although for example sputum usefully contains lung and upper respiratory-tract tissue DNA including DNA of lung cancers and upper respiratory-tract cancers, and feces usefully contains gastrointestinal tissue DNA including DNA of gastrointestinal-tract cancers, analysis of these DNAs are rendered difficult by the presence of bacteria and viruses in the lungs and upper respiratory tract in the case of sputum, or gastrointestinal microflora in the case of feces. Because the Alu retrotransposons are found only in primate DNA, the MIR retrotransposons are found only in mammals, and the SVA retrotransposons are found only in hominids, the use of Alu-, MIR- and SVA consensus sequence-based PCR primers to amplify human genomic DNA may provide a means to prepare human-specific amplicons even in the presence of bacterial and viral DNAs, if these DNAs are not amplified by such primers to an extent that interferes significantly with the sequence analysis of the human amplicons. It is therefore the objective of the present invention to develop and test the usefulness of this approach for analyzing human DNAs in microbial contaminated human exudates and excretions such as sputum and feces. Because sputum is known to contain cancer and precancer cells from the lungs and the upper respiratory-tract, and feces is known to contain gastrointestinal cancer cells, an ability to analyze their human DNA contents can expedite early cancer detection, and monitoring of the presence and/or alteration of cancer cells following cancer therapy.

A transposable element is a DNA sequence that can change its position within the genome of a single cell. Transposition can create phenotypically significant mutations that alter the cell's genome. The most common forms of transposable elements in humans are retrotransposons which include the Alu sequences, MIR sequences and SVA sequences, which are families of repetitive elements in the human genome. Generally, Alu elements are about 280 base pairs long, and MIR elements are about 145 base pairs long, both being classified as short interspersed elements ("SINEs") among the class of repetitive DNA elements. SVA elements are about 1000 base pairs long. There are about 1,080,000 replications of Alu sequences, 595,000 replications of MIR elements, and 3,700 replications of SVA elements in the human genome.

The term "Alu-element" as used herein encompasses a short stretch of DNA originally characterized by the action of the Alu (*Arthrobacter luteus*) restriction endonuclease. Alu elements of different kinds occur in large numbers in primate genomes. In fact, Alu elements are the most abundant transposable elements in the human genome. They are derived from the small cytoplasmic 7SL RNA, a component of the signal recognition particle. The typical structure of an Alu sequence is 5'-Part A-A5TACA6-Part B-PolyA Tail-3' (SEQ ID NO: 1). Because Part A and Part B are similar in nucleotide sequence, the structure suggests that modern human-Alu elements emerged from a fusion of two distinct fossil antique monomers over 100 million years ago. The length of the poly-A tail varies between Alu-families. Alu elements were first discovered in two major subfamilies known as AluJ and AluS, and other Alu subfamilies were soon discovered. Eventually a sub-subfamily of AluS that included active Alu elements was given the separate name AluY.

The term "MIR element" as used herein encompasses an ancient family of repeats the sequence divergence and common occurrence of which among placental mammals, marsupials and monotremes indicate their being abundant Mammalian-wide Interspersed Repeats, or MIRs. The typical structure of a MIR element consists of a tRNA-derived region containing a consensus RNA polymerase III promoter fused to an unrelated sequence. The tRNA-derived region bears similarity to the human Gln-tRNA-CUG gene.

The term "VNTR" as used herein represents Variable Number Tandem Repeat, and encompasses both microsatellites and minisatellites although not all tandem repeat domains are polymorphic in repeat copy number. The term "SVA element" as used herein encompasses the non-autonomous hominid retrotransposon family composed of SINE-VNTR-Alu. Because SVAs are currently active, they can generate genomic variations, and therefore potentially human traits, through a variety of mechanisms including mutational mutagenesis, exon shuffling, alternate splicing and production of differentially methylated regions.

Any observable parameter in the body dependent on the genotype is a phenotype, including molecules such as RNA and proteins. Most molecules and structures coded by the genetic material are not visible in the appearance of an organism, yet they are observable (for example by phenotypes such as cell morphologies) and are thus part of the phenotype. Human blood groups are an example of how phenotypes derived from genotypes can be expressed at the cellular level. Thus the genomic sequences and structure variations among humans may be employed to characterize the genotypic and hence phenotypic differences between human subjects. Within the same human subject, cells may also undergo somatic mutations that result in changes in genotypes and phenotypes, such as malignant mutations giving rise to cancers.

Massively parallel sequencing (MPS) technologies have transformed the landscape of genetics through their ability to produce giga-bases of sequence information in a single run. This technological advancement has cut down the cost of WGS, and it has been widely employed for trait-association and disease-association studies. However, its demand for relatively large amounts of DNA sample remains a major drawback. In most instances the use of even 3 micrograms of genomic DNA for analysis may not fully meet the stringent requirements of whole-genome sequencing. This microgram-plus DNA sample requirement becomes particularly difficult to fulfill in the case of human exudates and excretions where the total amount of human DNA present is usually limited.

In view of this, novel methods are needed to decrease the amount of sample DNA needed to produce high quality and relevant sequence data at a reduced cost. The Polymerase Chain Reaction ("PCR") technique allows a user to take a limited amount of starting genomic DNA and amplify enough DNA from various regions of the genome for sequence analysis. However, because the PCR amplification of huge numbers of sequences from different genomic regions requires the use of large numbers of costly PCR primers, methods have been developed to amplify selectively the ITE sequence segments between retrotransposons using only a small number of PCR primers based on for example the consensus sequences of Alu elements.

U.S. Pat. No. 5,773,649, titled "DNA markers to detect cancer cells expressing a mutator phenotype and method of diagnosis of cancer cell" and having Sinnett, et al. as inventors, was issued on Jun. 30, 1998 ("the Sinnett '649 Patent"). The Sinnett '649 Patent employed amplification with paired inter-Alu PCR primers followed by hybridization with a probe corresponding to an instability-prone locus and subjecting the amplified fragments to electrophoretic fractionation on a polyacrylamide gel to determine the presence of a variation in band profile between tumor and tumor-free DNA. This method of inter-Alu PCR only used a paired primer PCR system, which yielded a banded pattern of PCR amplicons in gel electrophoresis.

U.S. Pat. No. 7,537,889, titled "Assay for quantitation of human DNA using Alu elements" and having Sinha, et al. as inventors, was issued on May 26, 2009 ("the Sinha '889 Patent"). The Sinha '889 Patent employed amplification with paired inter-Alu PCR primers to determine the presence and quantity of human DNA in a sample in which non-human DNA may also be present. The assays were based on detection of multiple-copy Alu elements recently integrated into the human genome that are largely absent from non-human primates and other mammals. In the Sinha '889 Patent, use of inter-Alu PCR also only used a paired primer PCR system, which yielded a banded pattern of PCR amplicons in gel electrophoresis.

United States Patent Application No. 2015/0225722A1, titled "Methods for selective targeting of heterochromatin forming non-coding RNA" and having Ozsolak as inventor and dated Apr. 29, 2015, used oligonucleotides to modulate the heterochromatin status of genes regulated by non-coding RNAs. In some embodiments, such genes comprise triplet repeat regions or other repeat regions including Alu elements and MIR elements. The invention does not employ Alu-, MIR- or SVA-consensus sequences as PCR primers.

100141 The inventions described in the Sinnett'649 Patent and the Sinha'889 Patent utilized traditional PCR with paired primers based on consensus Alu-sequences to yield banded patterns of PCR amplicons. In a number of scientific studies (Kass and Batzer 1995; Walker et al 2003; Krajinovic et al 2012), Alu-based PCR was likewise employed in forensic casework to identify and quantitate human DNA in the presence of DNA from other species, based on the appearance of a human-specific amplicon band. However, in the scientific study of Mei, Ding, Xue et al (2011), inter-Alu PCR was employed to amplify a huge range of inter-Alu sequences from human genomic DNA followed by MPS analysis in order to generate a representative scan, viz. an AluScan, of genomic sequences. In order to enhance sequence diversity of the inter-Alu PCR amplicons, multiple PCR primers were used based on consensus sequences of Alu elements having both a Head-type (H-type) orientation such that primer extension proceeds beyond the head of the retrotransposon, and a Tail-type (T-type) orientation such that primer extension proceeds beyond the tail of the Alu retrotransposon. Such usage of both H-type and T-type primers made possible the production of a vast number of amplicons from sub-micrograms of DNA samples, resulting in smeared gel electrophoretograms instead of discrete bands upon DNA staining by ethidium bromide. Sequencing of these amplicons by means of MPS enabled the analysis of multitudinous numbers of sequence reads for examining DNA sequences from different locations in the human genome and their possible associations with human traits. The important utility of this AluScan method for capturing a huge number of genomic sequence segments as amplicons for MPS analysis, using only a small number of Alu-based PCR primers and submicrogram DNA template, was illustrated by the study of Kumar, Yang, Xue et al (2015) which revealed the massive occurrence of interstitial loss-of-heterozygosity mutations in cancers.

While the utility of the AluScan platform for amplifying and sequencing inter-Alu sequences derived from different regions of the human genome has been substantiated, Ng, Hu, Xue et al (2016) found that human genomic sequences are divisible into three different types of sequence zones based on the genomic features contained in the sequences: 45.1% of genomic sequences are in the genic zones enriched in genes, CpG islands, regulatory elements, methylation sites and Alu elements, 31.1% in the proximal zones enriched in enhancers, conserved indels and MIR elements, and 23.8% in the AT-rich distal zones. Both genic zones and proximal zones are functionally more important than the distal zones. However, insertions of Alu-element are preferentially located in the genic zones: the genic/proximal insertion ratio is 2.83 for AluJ, 2.82 for AluS and 2.04 for AluY. Consequently, the capture of inter-Alu sequences by AluScan using Alu-consensus sequence-based PCR primers is skewed in favor of genic zone sequences. In order to obtain a more balanced representation of the sequence and structure variations in both genic and proximal sequence zones, it becomes necessary to amplify genomic sequences using PCR primers based on not only the consensus sequences of Alu elements, but also the consensus sequences of another transposable element that is enriched in proximal zone segments. Since MIR elements are found in large numbers in the human genome and enriched in proximal zones, with a genic/proximal insertion ratio of 0.68, PCR amplification employing primers based on both Alu- and MIR-consensus sequences would yield inter-Alu, inter-MIR and inter-Alu-MIR amplicons with substantial coverage of both the genic and proximal sequence zones. In addition, the Alu- and MIR-based PCR primers employed for sequence capture can be further supplemented with PCR primers based on other retrotransposons to widen the range of coverage. In this regard, the SVA elements, occurring mainly in genic zones and only found in hominids, are among the youngest transposable elements in the human genome, and play important regulatory roles in the genome (Quinn and Bubb, 2014; Gianfrancesco, Bubb and Quinn, 2017). Therefore SVA-adjacent sequences are endowed with substantial potential for genomic variations associated with human traits, and SVA-based primers make an important source of ITE-PCR primers along with the Alu-based and MIR-based primers.

Thus, inter-Alu PCR employing both H-type and T-type Alu consensus sequence-based primers is capable of amplifying a huge number of inter-Alu amplicons for sequence analysis employing only submicrogram amounts of sample DNA. It is plausible that the same procedure may be employed to amplify a huge number of inter-MIR amplicons using MIR consensus sequence-based primers, to amplify a huge number of inter-SVA amplicons using SVA consensus sequence-based primers, and to amplify a huge number of inter-Alu, inter-MIR, inter-SVA, inter-inter-Alu-SVA and inter-MIR-SVA amplicons for sequence analysis using Alu consensus sequence-based, MIR consensus sequence-based and/or SVA consensus sequence-based PCR primers. The key question is whether or not such ITE-PCR amplifications employing Alu-, MIR- and/or SVA-based primers can usefully amplify human genomic DNA sequences for MPS analysis based on DNA samples from human exudates and excretions that are laden with bacterial and viral DNAs, which would interfere with the conventional protocols for human DNA sequencing.

BRIEF SUMMARY OF THE INVENTION

An array of inter-transposable-element polymerase chain reaction (ITE-PCR) amplicons of huge diversity in high yield can be obtained in high yield with submicrogram quantities of human DNA samples through the employment of Alu, MIR and SVA sequence-based PCR primers that comprise both Head-type primer that is extended during PCR through the head, and Tail-type primer that is extended through the tail, of the retrotransposon to which it is annealed. Performance of sequence analysis of these ITE-PCR amplicons using massively parallel sequencing (MPS) yields an 'AlmivaScan' of ITE-sequences that can include inter-Alu, inter-MIR, inter-SVA, inter-Alu-MIR, inter-Alu-SVA and inter-MR-SVA sequence segments from the genome. Because genomic sequence and structure variations such as single nucleotide polymorphisms, microsatellites, germline copy number variations and somatic copy number variations have been found in the present invention to be enriched to $p<0.01$ in the PCR-amplifiable vicinities of the Mu, MIR. and SVA retrotranposons, and personal and cellular traits are typically associated with genomic variations, an 'AlmivaScan' consisting of ITE-sequences provides an efficient basis for the discovery and analysis of associations between genomic sequence and structure variations on the one hand, and personal or cellular traits on the other including non-medical traits as well as diseased states, susceptibilities to diseases and responses to drugs. Because the Alu, MIR and SVA retrotransposable elements are absent from bacterial and viral DNAs, the present invention enables genomic analysis of human DNA samples, including samples of body exudates and excretions, with minimal interference from contaminating bacterial and viral DNAs.

In the present invention, human genomic DNA sequences are captured from the vicinities of Alu, MIR and SVA retrotransposons by ITE-PCR for genomic sequence analysis by MPS in a versatile 'AlmivaScan' methodological platform. The advantages of this methodological platform are threefold. First, Alu, MIR and SVA insertions are found in the present invention to be enriched near such genomic variations as single nucleotide polymorphisms (SNPs), microsatellites (MSTs), germline copy number variations (CNVGs) and somatic copy number variations (CNVTs); these genomic variations are useful for distinguishing between the inheritable traits of different human subjects, and detection of cells bearing genetic changes that are indicative of a disease genotype such as a cancerous or precancerous genotype. Secondly, the AlmivaScan platform is capable of producing ITE-PCR amplicons that give rise to a brightly ethidium bromide-stained and largely smeared gel electrophoretogram, indicative of the generation of a high yield of ITE genomic segments for sequence analysis. Thirdly, the methodological platform is found to be applicable to human DNA isolated from plasma, sputum as well as feces, which indicates that it provides a useful tool for analyzing human genomic sequences employing sample DNA isolated from human exudates and excretions that are laden with bacteria and viruses.

A method for identifying one or more genomic variations in human genomic DNA is provided. The method comprises forming an assay mixture. The assay mixture comprises a test sample comprising human genomic DNA; two or more primers; free deoxynucleotide triphosphates (dNTPs) comprising adenine (A), cytosine (C), guanine (G), and thymine (T) bases; a thermostable DNA polymerase; and a buffer solution. Each of the two or more primers comprises a consensus sequence based on the sequence of a transposable element (TE) or other repeating element found within the human genome. The TE or other repeating element is not typically found in microbial DNA, The method comprises performing a polymerase chain reaction (PCR) on the assay mixture to produce an array of amplicons comprising inter-transposable element (ITE) genomic segments.

A method for identifying one or more genomic variants associated with a trait or a disease is provided. The method comprises forming first and second assay mixtures. The first assay mixture comprises a first test sample comprising human genomic DNA, wherein the first test sample is obtained from a human subject having the trait or the disease. The first assay mixture further comprises two or more primers, wherein each primer comprises a consensus sequence based on the sequence of a transposable element (TE) or other repeating element found within the human genome. The TE or other repeating element is not typically found in microbial DNA. The first assay mixture also comprises free deoxynucleotide triphosphates (dNTPs)

comprising adenine (A), cytosine (C), guanine (G), and thymine (T) bases; a thermostable DNA polymerase; and a buffer solution. The second assay mixture comprises a second test sample comprising human genomic DNA, wherein the second test sample is obtained from a human subject that does not have the trait or the disease. The second assay mixture also comprises two or more primers, wherein the sequences of the two or more primers are identical to the sequences of the two or more primers in the first assay mixture. The second assay mixture additionally comprises free deoxynucleotide triphosphates (dNTPs) comprising adenine (A), cytosine (C), guanine (G), and thymine (T) bases; a thermostable DNA polymerase; and a buffer solution. The method comprises performing polymerase chain reactions (PCR) on each of the first and second assay mixtures to produce a first array of amplicons comprising inter-transposable element (VIE) genomic segments from the first test sample and a second array of amplicons comprising inter-transposable element (ITE) genomic segments from the second test sample.

An oligonucleotide is provided. The oligonucleotide comprises a nucleotide sequence selected from AGCTTGCAGTGAGCTGAGAT (SEQ ID NO: 6), GTCCGCAGTCCGGCCTGGGC (SEQ ID NO: 7), GATAGCGCCACTGCAGTCC (SEQ ID NO: 8), AGCCGAGATGGCAGCAGTA (SEQ ID NO: 11), and ACCAGAGACCTTTGTTCACT (SEQ ID NO: 12).

A kit for performing a polymerase chain reaction (PCR) on a test sample comprising human genomic DNA is provided. The kit comprises a first oligonucleotide primer and a second oligonucleotide primer, wherein the oligonucleotide primers comprise a nucleotide sequence selected from AGCTTGCAGTGAGTGAGAGAT (SEQ ID NO: 6), GTCCGCAGTCCGGCCTGGGC (SEQ ID NO: 7), GATAGCGCCACTGCAGTCC (SEQ ID NO: 8), AGCCGAGATGGCAGCAGTA (SEQ ID NO: 11), and ACCAGAGACCTTTGTTCACT (SEQ ID NO: 12), and the first and second oligonucleotide primers are different from one another. The kit also comprises instructions for using the first and second oligonucleotide primers in a PCR reaction for detecting genomic variations in human genomic DNA in a test sample comprising human genomic DNA.

Other objects and features will be in part apparent and in part pointed out hereinafter.

BRIEF DESCRIPTION OF DRAWINGS

Below are the descriptions of drawings and embodiments of the present invention.

FIG. 9 shows a table listing the distance intervals from various forms of human genomic polymorphisms within which enrichments of different retrotransposon groups to $p<0.01$ have been found. Subgroupings of retrotransposons were the same as described above for FIG. 3.

TABLE 1

| | |
|---|---|
| Lane A: | DNA M.W. Markers (from Fermentas) |
| Lane B: | 4-Alu Primers: AluY66H21 + AluY278T18 + L12A/8 + R12A/267 |
| Lane C: | MIL17 |
| Lane D: | 4-Alu Primers + MIL17 |
| Lane E: | MIR17 + MIL17 |
| Lane F: | 4-Alu Primers + MIR17 + MIL17 |
| Lane G: | SVAh + SVAt |
| Lane H: | 4-Alu Primers + SVAh + SVAt |
| Lane I: | AluYk4/k12 |
| Lane J: | 4-Alu Primers + AluYk4/k12 |
| Lane K: | AluYb8/b9 |
| Lane L: | 4-Alu Primers + AluYb8/b9 |
| Lane M: | AluYa5/a8 |
| Lane N: | 4-Alu Primers + AluYa5/a8 |
| Lane O: | 4-Alu Primers + MIL17 + SVAh + SVAt + AluYk4/k12 + AluYb8/b9 + AluYa5/a8 |
| Lane P: | 4-Alu Primers + MIR17 + MIL17 + SVAh + SVAt + AluYk4/k12 + AluYb8/b9 + AluYa5/a8 |

Figure 11:

FIG. 11 shows gel electrophoretograms of amplicons obtained by ITE-PCR in the presence of 12.5 ng of human sputum DNA using different sets of ITE-PCR primers. Lane A is an electrophoretogram of DNA molecular weight (M.W.) markers. Lanes B-P show electrophoretograms of ITE-PCR amplicons obtained using combinations of the ITE-PCR primers indicated in Table 1.

Figure 12:

FIG. 12 shows a gel electrophoretogram of amplicons obtained by ITE-PCR in the presence of 125 ng of human fecal DNA using different sets of ITE-PCR primers. Fecal sample was obtained following a 72-hour meat free diet. Lane A is an electrophoretogram of DNA molecular weight (M.W.) markers. Lanes B-P show electrophoretograms of ITE-PCR amplicons obtained using the combinations of ITE-PCR primers indicated in Table 1.

DETAILED DESCRIPTION OF THE INVENTION

Before describing the present invention in detail, it is to be understood that this invention is not limited to the employment of particular retrotransposon consensus sequence-based ITE-PCR primers for amplification of ITE-sequence segments, or particular compositions or procedures of the ITE-PCR process, which may vary. It is also to be understood that the terminology used herein is for the purpose of describing particular embodiments only, and is not intended to be limiting. In addition, before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications. Additionally, when examples are given, they are intended to be illustrative only and not to be restrictive.

It must be noted that, as used in this specification and the appended claims, the singular forms "a," "an" and "the" include plural referents unless the context clearly dictates otherwise. Thus, for example, reference to "a primer" may also include mixtures of two or more primers, and the like.

The terms "comprising", "including" and "having" are intended to be inclusive and mean that there may be additional elements other than the listed elements.

In describing and claiming the present invention, the following terminology will be used in accordance with the definitions set out below.

The term "PCR products" as used herein refers to PCR products generated from inter-transposable element PCR and treated with ethanol or other purification kits to remove any excess primers, enzymes, mineral oil, glycerol and salts.

Figure 1:
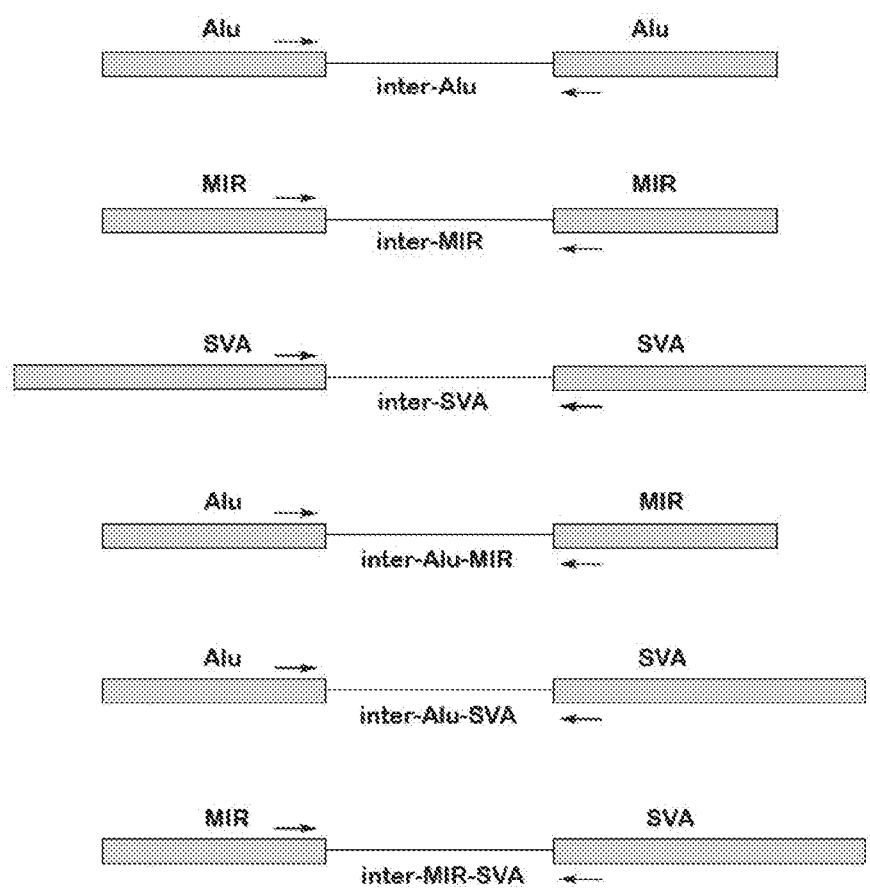
FIG. 1 shows an illustration of PCR amplification of an inter-transposable element (ITE) sequence segment (represented by a horizontal line) between two adjacent transposable elements (TEs) (represented by two rectangles) using two TE-consensus sequence-based primers one for the TE on the left and one for the TE on the right (represented by arrows). From top down: PCR of an inter-Alu segment between two Alu elements; PCR of an inter-MIR segment between two MIR elements; PCR of an inter-SVA segment between two SVA elements; PCR of an inter-Alu-MIR segment between an Alu and an MIR elements; PCR of an inter-Alu-SVA segment between an Alu and an SVA elements; and PCR of an inter-MIR-SVA segment between an MIR and an SVA elements.

The term "inter-transposable element sequence", viz. "ITE-sequence", as used herein refers to the DNA sequence segment positioned between two Alu elements, between two MIR elements, between two SVA elements, between one Alu element and one MIR element, between one Alu element and one SVA element, or between one MIR element and one SVA element (FIG. 1). PCR amplification of any ITE sequence segment using Alu-, MIR- and/or SVA-consensus sequences as primers is referred to as ITE-PCR. Since Alu and MIR elements are widespread in the human genome, with enrichment of Alu-elements in genic-zone sequences, and MIR-elements in proximal-zone sequences, ITE PCR using a combination of Alu- and MIR-consensus sequence-based primers can cover a significant albeit varied portion of the human genome, especially the highly functional genic- and proximal-zone sequences of the genome.

The term "quality" as used herein refers to two essential attributes of the ITE-PCR amplicons: the amount of amplicons produced using only nanogram-levels of human DNA sample, and the variety of different amplicons produced. The amount of amplicons produced has to be sufficient for sequencing using the MPS method; this is readily indicated by the brightness of ethidium bromide-stained DNA in a gel electrophoretogram of the amplicons upon ultraviolet (UV) illumination. The variety of different amplicons produced has to be sufficiently large in order to render MPS analysis of the PCR amplicons efficient and productive, which is readily indicated by an evidently smeared pattern of ethidium bromide-stained DNA largely with few distinct bands in a gel electrophoretogram of the amplicons.

The term "nanogram level of genomic DNA" as used herein refers to the submicrogram amounts of sample DNA needed for ITE-PCR followed by massively parallel sequencing.

The term "thermostable DNA polymerase" as used herein refers to the DNA polymerase used in ITE-PCR, which can be Taq polymerase, KOD polymerase or other polymerases used in DNA amplification.

The term "direction of amplification" as used herein refers to the direction of chain extension in PCR amplification proceeding forward through either the 5' (head) or 3' (tail) end of a transposable element (TE) annealed to by an ITE-PCR primer based on the consensus sequence of the TE. A primer is said to be 'head type' (H-type) if the direction of chain extension goes through the 5'-head of the TE, or 'tail type' (T-type) if the direction of chain extension goes through the 3'-tail of the TE, to which the primer is annealed.

Figure 2:
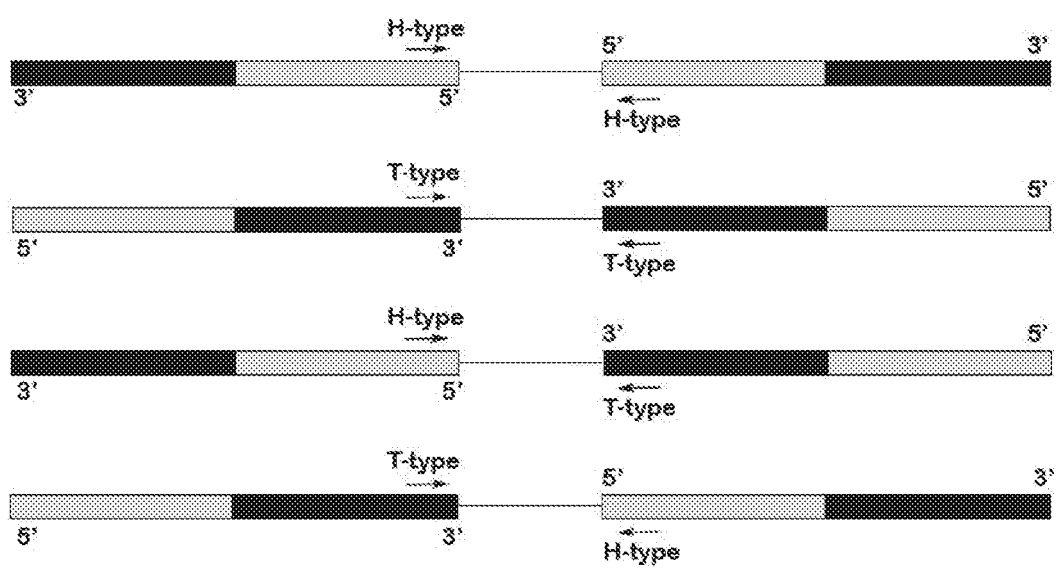
FIG. 2 shows an illustration of PCR amplification of an ITE sequence segment (represented by a horizontal line) between two adjacent TEs (represented by two rectangles) using two TE-consensus sequence-based primers, one for the TE on the left and one for the TE on the right (represented by two arrows). Each primer can be either H-type for chain extension through the head of a TE, or T-type for chain extension through the tail of a TE, in the course of PCR amplification. From top down: "head-to-head" amplification; "tail-to-tail" amplification; "head-to-tail" amplification; and "tail-to-head" amplification. Each of these four amplification modes can apply to the each of the six inter-transposable arrangements indicated in FIG. 1.
Figure 3:
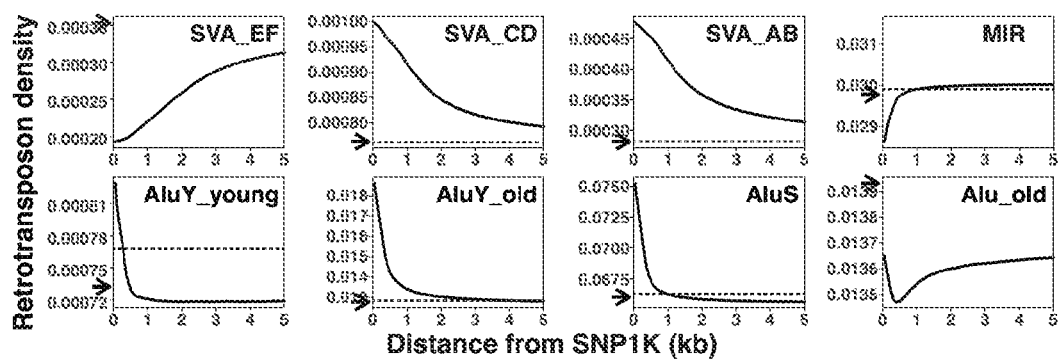
FIG. 3 shows an illustration of the density variations of retrotransposon groups at different distances from human single nucleotide polymorphisms (SNPs) in 1000-Genomes (SNP 1Ks). The average density of each retrotransposon group is plotted against the distance in kb (in 100 bp increments) between their locations and individual SNPs in "SNP1K" database. Arrow indicates genomic average density for the retrotransposon group. Densities above the dashed line are significantly enhanced to $p<0.01$ above the average density computed from random simulated placements of 1,000,000 SNPs (n=100x) using the Monte Carlo procedure (North et al 2002). Some of the retrotransposon subfamilies showing largely similar density patterns flanking the SNPs were grouped together: on this basis the six SVA subfamilies are separated into the SVA_EF group (SVA_E and SVA_F), SVA CD group (SVA_C and SVA_D), and SVA_AB group (SVA_A and SVA_B); the AluY subfamilies are separated into the AluY_young group (AluYa5, AluYb8, AluYb9, AluYh9, and AluYk12), and AluY_old group (AluY, AluYc, AluYc3, and AluYk4); and the Alu_old group comprises AluJb, AluJr4, and FLAM_A.
Figure 4:
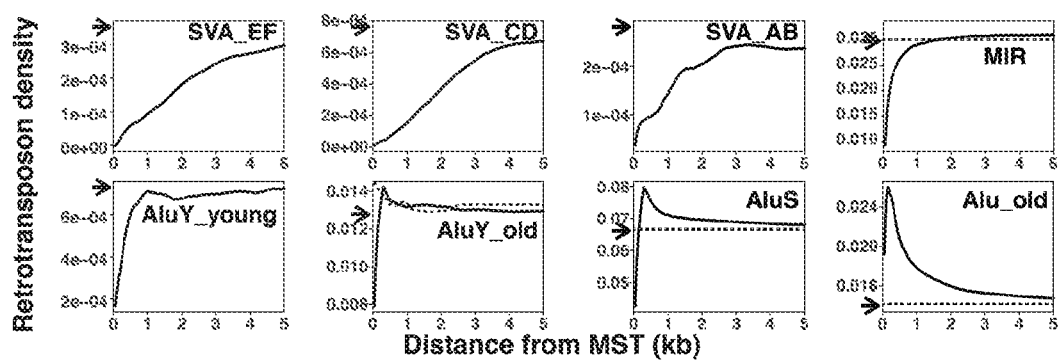
FIG. 4 shows an illustration of the density variations of retrotransposon groups at different distances from human microsatellites (MSTs). The average density of each retrotransposon group is plotted against the distance in kb (in 100 bp increments) between their locations and individual MSTs. Arrow indicates genomic average density for the retrotransposon group. Densities above the dashed line are significantly enhanced to $p<0.01$ above the average density computed from random simulated placements of the 41,572 MSTs in the genome (n=100x) using the Monte Carlo procedure (North et al 2002). Subgroupings of retrotransposons were the same as described above for FIG. 3.
Figure 5:
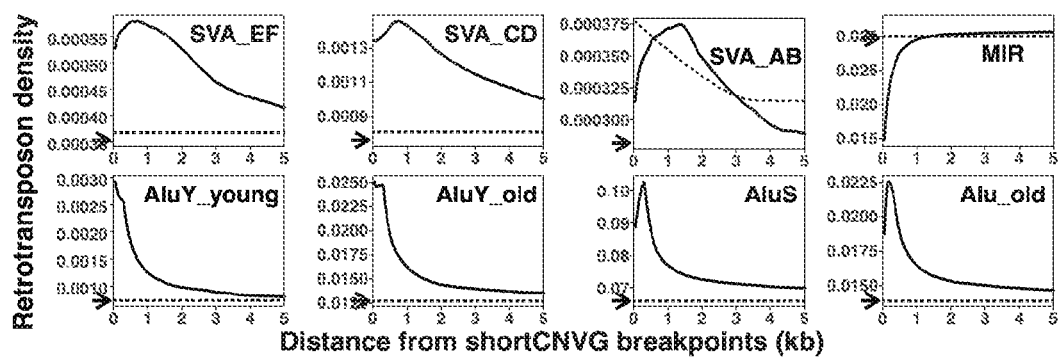
FIG. 5 shows an illustration of the density variations of retrotransposon groups at different distances from human short geitiiline copy number variations (shortCNVGs, viz. 5 bp<CNVGs≤158 bp). The average density of each retrotransposon group is plotted against the distance in kb (in 100 bp increments) between their locations and individual shortCNVGs. Arrow indicates genomic average density for the retrotransposon group. Densities above the dashed line are significantly enhanced to $p<0.01$ above the average density computed from random simulated placements of the 157,793 shortCNVGs in the genome (n=100x) using the Monte Carlo procedure (North et al 2002). Subgroupings of retrotransposons were the same as described above for FIG. 3.
Figure 6:
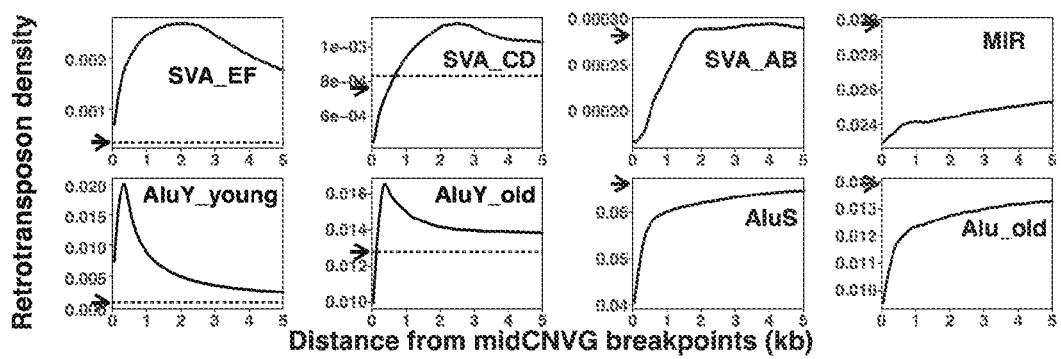
FIG. 6 shows an illustration of the density variations of retrotransposon groups at different distances from human germline midCNVGs (158 bp<CNVGs<15,848 bp). The average density of each retrotransposon group is plotted against the distance in kb (in 100 bp increments) between their locations and individual midCNVGs. Arrow indicates genomic average density for the retrotransposon group. Densities above the dashed line are significantly enhanced to $p<0.01$ above the average density computed from random simulated placements of the 350,037 midCNVGs in the genome (n=100x) using the Monte Carlo procedure (North et al 2002). Subgroupings of retrotransposons were the same as described above for FIG. 3.
Figure 7:
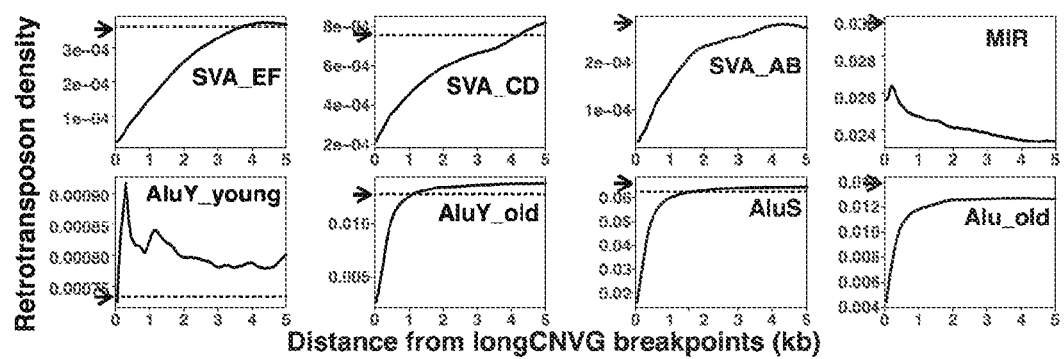
FIG. 7 shows an illustration of the density variations of retrotransposon groups at different distances from human germline longCNVGs (CNVGs>15848 bp). The average density of each retrotransposon group is plotted against the distance in kb (in 100 bp increments) between their locations and individual longCNVGs. Arrow indicates genomic average density for the retrotransposon group. Densities above the dashed line are significantly enhanced to $p<0.01$ above the average density computed from random simulated placements of the 256,085 longCNVGs in the genome (n=100x) using the Monte Carlo procedure (North et al 2002). Subgroupings of retrotransposons were the same as described above for FIG. 3.
Figure 8:
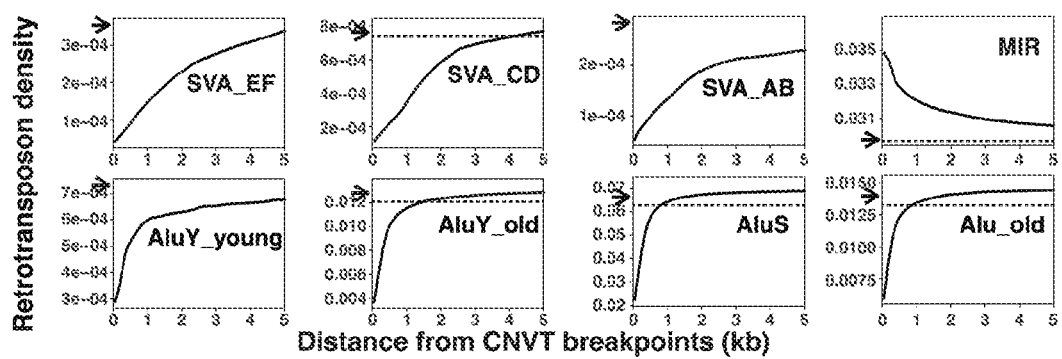
FIG. 8 shows an illustration of the density variations of retrotransposon groups at different distances from human somatic CNVs (CNVTs). The average density of each retrotransposon group is plotted against the distance in kb (in 100 bp increments) between their locations and individual CNVTs. Arrow indicates genomic average density for the retrotransposon group. Densities above the dashed line are significantly enhanced to $p<0.01$ above the average density computed from random simulated placements of the 985,038 CNVTs in the genome (n=100x) using the Monte Carlo procedure (North et al 2002). Subgroupings of retrotransposons were the same as described above for FIG. 3.

The term "head-to-head" as used herein refers to the amplification of an ITE segment between the 5' end of a TE and the 5' end of an adjacent TE (FIG. 2, top line).

The term "tail-to-tail" as used herein refers to the amplification of an ITE segment between the 3' end of a TE and the 3' end of an adjacent TE (FIG. 2, second line).

The term "head-to-tail" as used herein refers to the amplification of an ITE segment between the 5' end of a TE and the 3' end of an adjacent TE (FIG. 2, third line).

The term "tail-to-head" as used herein refers to the amplification of an ITE element segment between the 3' end of a TE and the 5' end of an adjacent TE (FIG. 2, fourth line).

The term "massively parallel sequencing" ("MPS") as used herein encompasses several high-throughput approaches to DNA sequencing; it is also called "next-generation sequencing" ("NGS"). These technologies use miniaturized and parallelized platforms for sequencing of 1-100 million short reads (50-400 bases). Many MPS platfoiiiis differ in engineering configurations and sequencing chemistry. However, they share the technical paradigm of massively parallel sequencing via spatially separated, clonally amplified DNA templates or single DNA molecules in a flow cell. This design is very different from that of Sanger sequencing, which is also known as capillary sequencing or first-generation sequencing that is based on electrophoretic separation of chain-terminated products produced in individual sequencing reactions.

The term "amplicon" as used herein refers to a piece of DNA formed as the product of natural or artificial amplification events. Most commonly, it can be formed via polymerase chain reactions ("PCR"). Conventionally, a particular set of ITE segments could be selectively amplified and evaluated in terms of the sizes of the fragments, which are usually visualized as a banded pattern in a gel electrophoretogram. Multi-primer ITE-PCR amplification leads to a vast array of ITE-amplicons having various sizes because they are amplified from genomic DNA regions having Alu-, MIR- and/or SVA-elements located within PCR-amplifiable distances from one another. The multi-primer ITE-PCR amplification products of this invention usually give rise to a banded pattern in an ethidium bromide-stained gel electrophoretogram when the number of inter-transposable element segments amplified are relatively few in number, or as a largely smeared non-banded pattern when the number of inter-transposable element segments amplified is so huge that the myriad of bands, produced from various head-to-head, tail-to-tail, head-to-tail and tail-to-head amplifications between adjacent Alu, MIR and/or SVA elements over different regions of the genome tend to merge together to produce a smear upon staining by ethidium bromide.

To test and verify the potential of an AlmivaScan to capture ITE-sequences enriched in genomic polymorphisms, analysis has been conducted in the present invention regarding the positions of Alu, MIR and SVA elements relative to the sites of such genomic polymorphisms as SNPs, MSTs, CNVGs and CNVTs. The results obtained, as shown in FIGS. 3-9, reveal that Alu, MIR and SVA elements are enriched to $p<0.01$ at specified PCR-amplifiable distances within 3 kb from polymorphic sites of SNPs, MSTs, CNVGs and CNVTs. These findings suggest that Alu, MIR and SVA insertions could be a significant factor in the induction of SNP, MST, CNVG and CNVT polymorphisms. In this regard, SNPs are known to be associated with Alu elements (Ng and Xue 2006), and with a variety of human traits and diseases (Batzer and Deininger 2002; Claussnitzer et al 2015; Fujimoto 2009; Kim 2012 et al; Kumar, Yang, Xue et al 2015; Lo, Lau, Xue et al 2004; Mbarek et al 2016; Medland et al 2016; Mei, Ding, Xue et al 2011; Sturm et al, 2005; Walker et al 2003; Zhao, Xu, Xue et al 2009). MSTs display a 2.7% genomic proportion of variable loci, much higher than SNP variations, modulate gene expressions, and are associated with human traits (Payseur et al 2011; Sawaya et al 2012; Bagshaw et al 2017); CNVGs are associated with human height and susceptibility to cancer (Li et al 2010; Ding, Tsang, Xue et al 2014); and CNVTs play an important role in central nervous system development, aging and cancer (Iourov et al 2008; Schlien and Malkin 2009). It therefore follows that PCR amplification of ITE-sequences using Alu-, MIR- and SVA-consensus sequence-based primers provides an efficient tool for capturing sites of polymorphisms for sequencing that are indicated by the findings in FIGS. 3-9 to be enriched with genomic polymorphisms, including polymorphisms that could represent the basis of various human traits.

To test the potential of an AlmivaScan platform for amplifying a high yield and huge variety of amplicons using ITE-PCR primers based on consensus sequences of Alu-, MIR- and SVA-retrotransposons, it was necessary to find illustrative sets of Alu-based, MIR-based and SVA-based primers that could generate amplicons in high yield, giving rise to gel electrophoretograms that are brightly stained by ethidium bromide, and comprise a huge variety of different amplicons, giving rise to a largely smeared-gel pattern instead of a mainly banded pattern. In this regard, the gel electrophoretograms illustrated in FIGS. 10-12 verified that combinations of Alu-, MIR- and SVA-based PCR primers could be found that gave rise to gel electrophoretograms of ITE-PCR amplicons that are both brightly stained by ethidium bromide and display a largely smeared gel pattern, indicating the amplification of a huge variety of different ITE-segments from the genome for MPS sequence analysis.

The method to identify relevant ITE genomic sequence segments associated with genetic differences between different DNA samples obtained from different subjects or from the same subject comprises: (a) selecting a paired set of discovery samples, wherein a genotype is expressed in the first set of the paired array and not the second set of the paired array; (b) amplifying an array of ITE genomic sequence segments for each of the paired set of discovery samples through ITE-PCR employing a selection of Alu-based, MIR-based and SVA-based ITE-PCR primers; (c) sequencing the array of ITE genomic sequence segments for each of the paired set of discovery samples using an MPS technique, thereby providing an 'AlmivaScan' of amplified ITE sequences from each sample; (d) storing the MPS results, viz. the AlmivaScans, for each paired set of discovery samples in a computer readable format; (e) identifying relevant ITE genomic sequence segments from the MPS results, viz. the AlmivaScans, where a genomic sequence or structure variation can be identified between the paired set of discovery samples, including but not limited to a single nucleotide polymorphism (SNP), single nucleotide variation (SNV), microsatellite (MST) or copy number variation (CNV).

Because the Alu elements are found only in primate genomes, MIR elements are found only in mammalian genomes, and SVA elements are found only in hominid genomes, the application of the 'AlmivaScan' platform to human genomic DNA sample would not be perturbed by the contamination of microbial DNA or plant DNA in the sample. In addition, when the human DNA sample is taken from a subject that has been sustained on for example a 72-hour diet free of foods containing any beef, pork, lamb or any other mammalian ingredients, the human genomic DNA sample also will only be minimally perturbed by contamination of any animal DNA in the sample. Accordingly, 'AlmivaScan' analysis will be applicable not only to the blood or tissue samples of human subjects but also samples obtained from feces, sputum, oral cavity etc. In view of this, one embodiment of the present invention is based on DNA sample obtained from human white blood cells. Another embodiment of the present invention is based on DNA sample obtained from human sputum. Yet another embodiment of the present invention is based on DNA sample obtained from human feces. The sputum DNA sample would be open to microbial contamination from the lungs and respiratory tract, and the fecal DNA sample would be open to microbial contamination from the gastrointestinal system.

A core advantage of the AlmivaScan sequencing platform stems from the large numbers of Alu and MIR insertions in the human genome, with enrichment of Alu in genic-zone sequences and MIR in the proximal-zone sequences, as a result of which ITE-PCR employing primers that include Alu- and MIR-consensus sequence-based primers can amplify a huge a variety of ITE-amplicons from the human genome. As a result, although SVA insertions are relatively fewer in numbers, amplification of SVA-adjacent sequences can be augmented through the amplification of not only inter-SVA sequences, but also through the amplification of inter-Alu-SVA and inter-MIR-SVA sequences (FIG. 1). Furthermore, this advantage can be extended to other transposable element(s) in general (or GTE) besides SVA with also relatively fewer insertions in the human genome, provided that the GTE sequence is generally absent from microbial DNA. By using a combination of Alu-, MIR- and GTE-consensus sequence-based ITE-PCR primers, amplification of GTE-adjacent sequences can be augmented through the amplification of not only inter-GTE sequences, but also through the amplification of inter-Alu-GTE and inter-MIR-GTE sequences.

A method of sequence analysis is provided. The method uses multiple inter-transposable element (ITE)-PCR primers to amplify ITE-sequences for sequencing with the objective of discovery and/or analysis of associations between sequence and structure variations in the human genome and personal or cellular traits including diseased states, susceptibilities to diseases and responses to drugs. The method comprises:

(a) performing ITE-PCR using the following PCR reaction mixture of components:
  i. two or more Alu consensus sequence-based, MIR consensus sequence-based, and/or SVA consensus sequence-based ITE-PCR primers;
  ii. a human genomic DNA sample; and
  iii. a PCR-extension mix comprising:
    a set of free deoxynucleotide triphosphates with A, G, T and C bases;
    a thermostable DNA polymerase; and
    a buffer solution;
(b) completing an ITE-PCR amplification program with the PCR reaction mixture in a PCR machine for a period of time to produce an array of inter-Alu, inter-MIR, inter-SVA, inter-Alu-MIR, inter-Alu-SVA and/or inter-MIR-SVA amplicons;
(c) performing sequence analysis on the array of inter-Alu, inter-MIR, inter-SVA, inter-Alu-MIR, inter-Alu-SVA and/or inter-MIR-SVA amplicons using a massively parallel sequencing procedure; and
(d) comparing the sequence-analysis results on test DNA samples and control DNA samples derived from the same or different subjects, in order to determine the correlations between genomic sequence variations on the one hand, and personal or cellular traits on the other hand.

One or more of the ITE-PCR primers can be based on the consensus sequences of retrotransposon(s) or repeating sequences other than the Alu, MIR and SVA retrotransposons, provided that the other repeating sequences are generally absent from microbial DNA.

The DNA sample can be prepared from human white blood cells.

The DNA sample can be prepared from human sputum.
The DNA sample can be prepared from human feces.
The DNA sample can be prepared from human plasma.
The DNA sample can be prepared from human serum.
The DNA sample can be prepared from human urine.
The DNA sample can be prepared from human saliva.
The DNA sample can be prepared from any human tissue besides white blood cells, plasma and serum.

The DNA sample can be prepared from any exudate or excretion besides sputum, feces, urine and saliva.

In any of the methods, a relevant inter-ITE sequence polymorphism can be associated with a personal trait or cellular trait or disease, as follows:

(a) selecting a paired set of discovery samples, wherein the trait is expressed in the first of the paired samples and not in the second of the paired samples;
(b) generating an array of ITE sequence segments for each of the paired set of discovery samples;
(c) sequencing the array of ITE sequence segments for each of the paired set of discovery samples using massively parallel sequencing technique forming a massively parallel ITE sequence pattern;
(d) transforming a massively parallel ITE sequence pattern for each paired set of discovery samples to a computer readable format; and
(e) identifying relevant ITE sequence elements from the massively parallel ITE sequence patterns where the presence of an identifiable genetic variation between the paired set of discovery samples is detected, so that the relevant ITE sequence element is identified as being associated with the trait.

The method can further comprise the step of identifying relevant ITE sequence segments from the massively parallel ITE sequence patterns where an identifiable genetic variation between the paired set of discovery samples is represented by a threshold read quality score at variant base(s).

The method can further comprise the step of identifying relevant ITE sequence segments from the massively parallel ITE sequence patterns where an identifiable genetic variation between the paired set of discovery samples is represented by alignment with a threshold value of importance to a homeostasis marker of the trait.

The method can further comprise the step of identifying relevant ITE sequence segments from the massively parallel ITE sequence patterns where an identifiable genetic variation between the paired set of discovery samples is represented by alignment with a threshold value of trait severity.

The method can further comprise the step of selecting an identifiable genetic variation between the paired set of discovery samples in the form of a loss of heterozygosity.

The method can further comprise the step of selecting an identifiable genetic variation between the paired set of discovery samples in the form of a somatic indel.

The method can further comprise the step of selecting an identifiable genetic variation between the paired set of discovery samples in the form of a single nucleotide variation ("SNV").

The method can further comprise the step of selecting an identifiable genetic variation between the paired set of discovery samples in the form of a frameshift variant.

In any of the methods, the novel DNA primer with the sequence of 5'-AGCTTGCAGTGAGCTGAGAT-3' (SEQ ID NO: 6) can be employed as one of the ITE-PCR primers.

In any of the methods, the novel DNA primer with the sequence of [5'-GTCCGCAGTCCGGCCTGGGC-3'] (SEQ ID NO: 7) can be employed as one of the ITE-PCR primers.

In any of the methods, the novel DNA primer with the sequence of [5'-GATAGCGCCACTGCAGTCC-3'] (SEQ ID NO: 8) can be employed as one of the ITE-PCR primers.

In any of the methods, the novel DNA primer with the sequence of [5'-AGCCGAGATGGCAGCAGTA-3] (SEQ ID NO: 11) can be employed as one of the ITE-PCR primers.

In any of the methods, the novel DNA primer with the sequence of [5'-ACCAGAGACCTTTGTTCACT-3'] (SEQ ID NO: 12) can be employed as one of the ITE-PCR primers.

A method for identifying one or more genomic variations in human genomic DNA is provided. The method comprises forming an assay mixture. The assay mixture comprises a test sample comprising human genomic DNA; two or more primers; free deoxynucleotide triphosphates (dNTPs) comprising adenine (A), cytosine (C), guanine (G), and thymine (T) bases; a thermostable DNA polymerase; and a buffer solution. Each of the two or more primers comprises a consensus sequence based on the sequence of a transposable element (TE) or other repeating element found within the human genome. The TE or other repeating element is not typically found in microbial DNA. The method comprises performing a polymerase chain reaction (PCR) on the assay mixture to produce an array of amplicons comprising inter-transposable element (ITE) genomic segments.

The method can further comprise sequencing the amplicons using high-throughput DNA sequencing.

The method can further comprises comparing the sequences of the amplicons to a sequence from the same region of the human genome in a control DNA sample to identify one or more genomic variations between the test sample and the control DNA sample.

The control DNA sample can be a genomic DNA sample taken from a human subject and sequenced by any method known in the art. Alternatively, the control DNA sample can be a known human genomic DNA sequence.

A method for identifying one or more genomic variants associated with a trait or a disease is provided. The method comprises forming first and second assay mixtures. The first assay mixture comprises a first test sample comprising human genomic DNA, wherein the first test sample is obtained from a human subject having the trait or the disease. The first assay mixture further comprises two or more primers, wherein each primer comprises a consensus sequence based on the sequence of a transposable element (TE) or other repeating element found within the human genome. The TE or other repeating element is not typically found in microbial DNA. The first assay mixture also comprises free deoxynucleotide triphosphates (dNTPs) comprising adenine (A), cytosine (C), guanine (G), and thymine (T) bases; a thermostable DNA polymerase; and a buffer solution. The second assay mixture comprises a second test sample comprising human genomic DNA, wherein the second test sample is obtained from a human subject that does not have the trait or the disease. The second assay mixture also comprises two or more primers, wherein the sequences of the two or more primers are identical to the sequences of the two or more primers in the first assay mixture. The second assay mixture additionally comprises free deoxynucleotide triphosphates (dNTPs) comprising adenine (A), cytosine (C), guanine (G), and thymine (T) bases; a thermostable DNA polymerase; and a buffer solution. The method comprises performing polymerase chain reactions (PCR) on each of the first and second assay mixtures to produce a first array of amplicons comprising inter-transposable element (ITE) genomic segments from the first test sample and a second array of amplicons comprising inter-transposable element (ITE) genomic segments from the second test sample.

The method can further comprises sequencing the first and second arrays of amplicons using high-throughput DNA sequencing.

The method can further comparing the sequences of the first array of amplicons to the sequences of the second array of amplicons and identifying one or more genomic variations between the first and second test samples, wherein the presence of a genomic variation in the first test sample but not in the second test sample indicates that the genomic variation may be associated with the trait or disease.

A kit for performing a polymerase chain reaction (PCR) on a test sample comprising human genomic DNA is provided. The kit comprises a first oligonucleotide primer and a second oligonucleotide primer, wherein the oligonucleotide primers comprise a nucleotide sequence selected from AGCTTGCAGTGAGCTGAGAT (SEQ ID NO: 6), GTCCGCAGTCCGGCCTGGGC (SEQ ID NO: 7), GATAGCGCCACTGCAGTCC (SEQ ID NO: 8), AGCCGAGATGGGCAGCAGTA (SEQ ID NO: 11), and ACCAGAGACCTTTGTTCACT (SEQ ID NO: 12), and the first and second oligonucleotide primers are different from one another. The kit also comprises instructions for using the first and second oligonucleotide primers in a PCR reaction for detecting genomic variations in human genomic DNA in a test sample comprising human genomic DNA.

The kit can further optionally comprise other components needed for carrying out the PCI reaction, e.g., a thermostable DNA polymerase; free deoxynucleotide triphosphates (dNTPs) comprising adenine (A), cytosine (C), guanine (G), and thymine (T) bases; and/or a buffer solution.

In any of the methods or kits, the genomic variation can comprises a single nucleotide polymorphism (SNP), a microsatellite (MST), a germline copy number variation (CNVG) (e.g., a short CNVG, a mid CNVG, a long CNVG, or a combination of any thereof), a somatic copy number variation (CNVT), or a combination of any thereof.

The test sample can comprise any human tissue, exudate, or excretion.

The test sample, the first test sample, and/or the second test sample can comprise human white blood cells.

The test sample, the first test sample, and/or the second test sample can comprise human sputum.

The test sample, the first test sample, and/or the second test sample can comprise human feces. Where the test sample, the first test sample, and/or the second test sample comprises human feces, the feces are preferably obtained from a human subject who has consumed a diet free of mammalian meat or tissue for at least about 72 hours prior to collection of the test sample.

The test sample, the first test sample, and/or the second test sample can comprise human plasma.

The test sample, the first test sample, and/or the second test sample can comprise human serum.

The test sample, the first test sample, and/or the second test sample can comprise human urine.

The test sample, the first test sample, and/or the second test sample can comprise human saliva.

The test sample, the first test sample, and/or the second test sample can comprise any combination of human white blood cells, human sputum, human feces, human plasma, human serum, human urine, human saliva.

The test sample, the first test sample, and/or the second test sample can comprises a sub-microgram quantity of human DNA.

The test sample, the first test sample, and/or the second test sample can further comprises microbial DNA, plant DNA, non-human animal DNA, or a combination of any thereof.

The test sample, the first test sample, and/or the second test sample can further comprise microbial DNA, plant DNA, or both microbial DNA and plant DNA. A human fecal sample would typically contain large amounts of both microbial and plant DNA.

The test sample, the first test sample, and/or the second test sample: can further comprise microbial DNA.

Where the test sample, the first test sample, and/or the second test sample contains microbial :DNA and/or plant DNA, the microbial and/or plant DNA can be present in the sample in a high amount without interfering with the assay results. For example, the ratio of microbial and/or plant DNA to human DNA in the test sample, the first test sample, or the second test sample, can be between 0.1:1 and 100:1, for example 1:1 and 50:1 or between 2:1 and 10:1.

Each of the two or more primers comprises a consensus sequence based on the sequence of a transposable element (TE) found within the human genome, wherein the TE is not typically found in microbial DNA.

For example, each of the two or more primers can comprise a consensus sequence based on an Alu-element, a consensus sequence based on a MIR element, or a consensus sequence based on an SVA element.

For example, the assay mixture, the first assay mixture, and/or the second assay mixture can comprise at least one primer comprising a consensus sequence based on an Alu element and at least one primer comprising a consensus sequence based on a MIR element.

The assay mixture, the first assay mixture, and/or the second assay mixture can comprise at least one primer comprising a consensus sequence based on an Alu element and at least one primer comprising a consensus sequence based on an SVA element.

The assay mixture, the first assay mixture, and/or the second assay mixture can comprise at least one primer comprising a consensus sequence based on a MIR element and at least one primer comprising a consensus sequence based on an SVA element;

The assay mixture, the first assay mixture, and/or the second assay mixture can comprise at least two primers comprising a consensus sequence based on a MIR element.

The assay mixture, the first assay mixture, and/or the second assay mixture can comprise at least two primers comprising a consensus sequence based on a SVA element.

The assay mixture, the first assay mixture, and/or the second assay mixture can comprise at least one primer comprising a consensus sequence based on an Alu element.

The assay mixture, the first assay mixture, and/or the second assay mixture preferably comprises two or more primers each comprising a consensus sequence based on an Alu element.

The assay mixture, the first assay mixture, and/or the second assay mixture even more preferably comprises two or more primers each comprising a consensus sequence based on an Alu element, and one or more primers each comprising a consensus sequence based on an MIR element.

The assay mixture, the first assay mixture, and/or the second assay mixture even more preferably comprises two or more primers each comprising a consensus sequence based on an Alu element, and one or more primers each comprising a consensus sequence based on an SVA element.

The assay mixture, the first assay mixture, and/or the second assay mixture even most preferably comprises at least four or more primers each comprising a consensus sequence based on an Alu element, at least one or more primers each comprising a consensus sequence based on an MIR element, and at least one or more primers each comprising a consensus sequence based on an SVA element.

At least one of the primers can comprise a consensus sequence based on an Alu-element.

Where at least one of the primers comprises a consensus sequence based on an Alu-element, the primer can comprise a nucleotide sequence selected from TGGTCTCGATCFC-CIGACCIC (SEQ ID NO: 2), GAGCGA-GACTCCGTCTCA (SEQ ID NO: 3), TGAGCCACCGCG (SEQ ID NO: 4), AGCGAGACTCCG (SEQ ID NO: 5), AGCTTGCAGTGAGCTGAGAT (SEQ II) NO: 6), GTCCGAGTCCCGCCTGGGC (SEQ NO: 7), and GATAGCGCCACTGCAGTCC (SEQ ID NO: 8).

Where at least one of the primers comprises a consensus sequence based on an Alu-element, the primer can comprise the nucleotide sequence AGCTTGCAGTGAGCTGAGAT (SEQ ID NO: 6).

Where at least one of the primers comprises a consensus sequence based on an Alu-element, the primer can comprise the nucleotide sequence GTCCGCAGTCCGGCCTGGGC (SEQ ID NO: 7).

Where at least one of the primers comprises a consensus sequence based on an Alu-element, the primer can comprise the nucleotide sequence GATAGCGCCACTGCAGTCC (SEQ ID NO: 8).

At least one of the primers can comprise a consensus sequence based on a MIR element.

Where at least one of the primers comprises a consensus sequence based on a MIR element, the primer can comprise a nucleotide sequence selected from AGTGACTTGCTAAGGT (SEQ ID NO: 9) and GCCTCAGTTTCCTCATC (SEQ ID NO: 10).

At least one of the primers can comprise a consensus sequence based on an SVA element.

Where at least one of the primers comprises a consensus sequence based on an SVA element, the primer can comprise the nucleotide sequence AGCCGAGATGGCAGCAGTA (SEQ. ID NO: 11).

Where at least one of the primers comprises a consensus sequence based on an SVA element, the primer can comprise the nucleotide sequence ACCAGAGACCTFTGTTCACT (SEQ ID NO: 12).

The assay mixture, the first assay mixture, and/or the second assay mixture can comprise three or more primers.

The assay mixture, the first assay mixture, and/or the second assay mixture can comprise four or more primers.

The assay mixture, the first assay mixture, and/or the second assay mixture can comprise five or more primers.

The assay mixture, the first assay mixture, and/or the second assay mixture can comprise six or more primers.

The assay mixture, the first assay mixture, and/or the second assay mixture can comprise seven or more primers.

The assay mixture, the first assay mixture, and/or the second assay mixture can comprise eight or more primers.

The assay mixture, the first assay mixture, and/or the second assay mixture can comprise nine or more primers.

The assay mixture, the first assay mixture, and/or the second assay mixture can comprise ten or more primers.

The assay mixture, the first assay mixture, and/or the second assay mixture can comprise eleven or more primers.

The assay mixture, the first assay mixture, and/or the second assay mixture can comprise at least five primers, wherein the primers comprise the nucleotide sequences of SEQ ID NOs. 2, 3, 4, 5, and 9.

The assay mixture, the first assay mixture, and/or the second assay mixture can comprise at least six primers, wherein the primers comprise the nucleotide sequences of SEQ ID NOs. 2, 3, 4, 5, 11, and 12.

The assay mixture, the first assay mixture, and/or the second assay mixture can comprise at least five primers, wherein the primers comprise the nucleotide sequences of SEQ ID NOs. 2, 3, 4, 5, and 8.

The assay mixture, the first assay mixture, and/or the second assay mixture can comprise at least five primers, wherein the primers comprise the nucleotide sequences of SEQ ID NOs. 2, 3, 4, 5, and 7.

The assay mixture, the first assay mixture, and/or the second assay mixture can comprise at least five primers, wherein the primers comprise the nucleotide sequences of SEQ NOs. 2, 3, 4, 5, and 6.

The assay mixture, the first assay mixture, and/or the second assay mixture can comprise at least six primers, wherein the primers comprise the nucleotide sequences of SEQ ID NOs. 2, 3, 4, 5, 9, and 10.

The assay mixture, the first assay mixture, and/or the second assay mixture can comprise at least ten primers, wherein the primers comprise the nucleotide sequences of SEQ ID NOs. 2, 3, 4, 5, 6, 7, 8, 9, 11, and 12.

The assay mixture, the first assay mixture, and/or the second assay mixture can comprise at least eleven primers, wherein the primers comprise the nucleotide sequences of SEQ ID NOs. 2, 3, 4, 5, 6, 7, 8, 9, 10, 11, 12.

The primers preferably comprise at least one primer having a head-type (H-type) orientation, such that primer extension proceeds beyond the head of the transposable element or other repeating element; and at least one primer having a tail-type (T-type) orientation, such that primer extension proceeds beyond the tail of the transposable element or other repeating element.

The inter-transposable element (ITE) genomic segments can comprise inter-Alu segments, inter-MIR segments, inter-SVA segments, inter-Alu-MIR segments, inter-Alu-SVA segments, inter-MIR-SVA segments, or a combination of any thereof.

The high-throughput DNA sequencing can comprise massively parallel sequencing.

The massively parallel sequencing can produce a massively parallel inter-transposable element (FE) sequence pattern.

The method can further comprise transforming the data obtained from the sequencing into a computer-readable format prior to comparing the sequences of the amplicons to the sequence of the control DNA sample.

The method can further comprise transforming the data obtained from the sequencing into a computer-readable format prior to comparing the sequences of the first array of amplicons to the sequences of the second array of amplicons.

The method can further comprise identifying relevant ITE genomic segments from the massively parallel inter-transposable (ITE) element sequence pattern, wherein the presence of a genetic variation between the first and second test samples is represented by a threshold read quality score at variant base(s).

The method can further comprise identifying relevant ITE genomic segments from the massively parallel inter-transposable (ITE) element sequence pattern, wherein the presence of a genetic variation between the first and second test samples is represented by alignment with a threshold value of importance to a homeostasis marker of the trait or disease.

The method can further comprise identifying relevant ITE genomic segments from the massively parallel inter-transposable (ITE) element sequence pattern, wherein the presence of a genetic variation between the first and second test samples is represented by alignment with a threshold value of trait or disease severity.

The genetic variation between the first and second test samples comprises a loss of heterozygosity.

The genetic variation between the first and second test samples comprises a somatic indel.

The genetic variation between the first and second test samples comprises a single nucleotide polymorphism.

An oligonucleotide is provided. The oligonucleotide comprises a nucleotide sequence selected from AGCTRICAGT-GAGCTGAGAT (SEQ II) NO: 6), GTCCGCAGTCCGGCCTGGGC (SEQ ID NO: 7), GATAGCGCCACTGCAGTCC (SEQ ID NO: 8), AGCCGAGATGGCAGTA (SEQ ID N˜0: 11), and ACCAGAGACCTTTGTTCACT (SEQ ID NO: 12).

Having described the invention in detail, it will be apparent that modifications and variations are possible without departing from the scope of the invention defined in the appended claims.

EXAMPLES

The following non-limiting examples are provided to further illustrate the present invention.

Example 1

Relative locations of single nucleotide polymorphisms (SNPs) and Alu, MIR and SVA retrotranposons. To examine the possible correlations between the Alu, MIR and SVA retrotransposons and SNPs, the locations of these retrotransposons from UCSC table browser RepeatMasker track for human assembly hg19 (Smit et al 2010) were compared to the locations of entries in SNP1K database. The graphs in FIG. 3 and the summary in FIG. 9 show that the densities of SVA_CD and SVA_AB elements at distances up to 5 kb, MIR at 1-5 kb, AluY-young at up to 0.25 kb, AluY old at up to 3.7 kb, and AluS at up to 0.95 kb from SNP1K entries are enriched to p<0.01 compared to randomized Monte Carlo simulations (n=100x) of 100M SNPs within 22 autosomes.

Example 2

Relative locations of microsatellites (MSTs) and Alu, MIR and SVA retrotranposons. To examine the possible correlations between the Alu, MIR and SVA retrotransposons and MSTs, the locations of these retrotransposons from UCSC table browser RepeatMasker track for human assembly hg19 (Smit et al 2010) were compared to the locations of entries in the MST database. The graphs in FIG. 4 and the summary in FIG. 9 show that the densities of MIR elements at 1.65-5 kb, AluY old at 0.3-0.75 kb and 1.05-2.35 kb, AluS at 0.2 –5 kb, and Alu old at up to 5 kb from MST entries are enriched to p<0.01 compared to randomized Monte Carlo simulations (n=100x) of all MST entries within 22 autosomes.

Example 3

Relative locations of short germline copy number variations (shortCNVs) and Alu, MIR and SVA retrotranposons. To examine the possible correlations between the Alu, MIR and SVA retrotransposons and shortCNVs, the locations of these retrotransposons from UCSC table browser RepeatMasker track for human assembly hg19 (Smit et al 2010) were compared to the locations of shortCNVG entries in the deVars database (5 bp<CNVG<158 bp). The graphs in FIG. 5 and the summary in FIG. 9 show that the densities of SVA EF, SVA CD, AluY young, AluY old, AluS and Alu old at up to 5 kb, SVA AB at 0.6-2.95 kb, and MIR at 1.4-5 kb from shortCNVG entries are enriched to p<0.01 compared to randomized Monte Carlo simulations (n=100x) of all shortCNVG entries within 22 autosomes.

Example 4

Relative locations of midsized germline copy number variations (midCNVGs) and Alu, MIR and SVA retrotransposons. To examine the possible correlations between the Alu, MIR and SVA retrotransposons and midCNVGs, the locations of these retrotransposons from UCSC table browser RepeatMasker track for human assembly hg19 (Smit et al 2010) were compared to the locations of midCNVG entries in the dbVars database (158 bp<CNVG<15848 bp). The graphs in FIG. 6 and the summary in FIG. 9 show that the densities of SVA_EF and AluY_young at up to 5 kb, SVA_CD at 0.7-5 kb and AluY old at 0.15-5 kb from midCNVG entries are enriched to p<0.01 compared to randomized Monte Carlo simulations (n=100x) of all midCNVG entries within 22 autosomes.

Example 5

Relative locations of long germline copy number variations (longCNVGs) and Alu, MIR and SVA retrotranposons. To examine the possible correlations between the Alu, MIR and SVA retrotransposons and longCNVGs, the locations of these retrotransposons from UCSC table browser RepeatMasker track for human assembly hg19 (Smit et al 2010) were compared to the locations of longCNVG entries in the dbVars database (CNVG>15848 bp). The graphs in FIG. 7 and the summary in FIG. 9 show that the densities of SVA_EF at 3.75-5 kb, SVA_CD at 4.25-5 kb, AluY young at 0.15 kb, AluY old at 0.9-5 kb and AluS at 1.7-5 kb from longCNVG entries are enriched to p<0.01 compared to randomized Monte Carlo simulations (n=100x) of all longCNVG entries within 22 autosomes.

Example 6

Relative locations of somatic copy number variations (CNVTs) and Alu, MIR and SVA retrotranposons. To examine the possible correlations between the Alu, MIR and SVA retrotransposons and CNVTs, the locations of these retrotransposons from UCSC table browser RepeatMasker track for human assembly hg19 (Smit et al 2010) were compared to the locations of CNVT entries in the COSMIC database (Forbes et al 2015). The graphs in FIG. 8 and the summary in FIG. 9 show that the densities of SVA CD at 4.15-5 kb, MIR at up to 5 kb, AluY old at 1.5-5 kb, AluS at 0.8-5 kb and Alu old at 0.85-5 kb from CNVT entries are enriched to p<0.01 compared to randomized Monte Carlo simulations (n=100x) of all CNVTs entries within 22 autosomes.

The results of Examples 1-6, plotted in the graphs in FIGS. 3-8, show that statistical enrichments of Alu, MIR and SVA insertions to p<0.01 were observed over various specified distance intervals from the sites of SNPIK, MST, shortCNCG, midCNVG, longCNVG and CNVT polymorphisms. These enrichments suggest that chromosomal instabilities brought about by the retrotransposon insertions in the course of human genome evolution have favored the appearance of genotypic polymorphisms in the neighborhood of the insertions. While some of these genotypic differences are phenotypically silent, others lead to phenotypic differences between individuals that come to be recognized as human traits. The enrichments of Alu, MIR and SVA within the PCR-amplifiable distances of –3 kb from SNPs, MSTs, CNVGs and CNVTs, summarized in FIG. 9, verified the utility and efficiency of using ITE-PCR with Alu-, MIR- and SVA-consensus sequence-based primers for capturing for massively parallel sequencing (MPS) the sites of genomic polymorphisms that can be associated with human traits.

Example 7

The utility of an AlmivaScan sequencing platform, whereby Alu-, MIR- and SVA-consensus sequence-based ITE-PCR primers are employed to generate ITE-PCR amplicons for sequence analysis by means of MPS, depends on the quality of the amplicons. The requisite quality of the amplicons refers to two attributes, viz. a high yield of amplicons to enable in-depth sequencing by MPS, which is to be indicated by intense brightness of ethidium bromide-stained DNA in a gel electrophoretogram of the amplicons upon ultraviolet (UV) illumination, and a huge variety of amplicons that can provide a wide range of Alu-, MIR- and SVA-adjacent sequences for MPS analysis, which is to be indicated by a largely smeared gel pattern of ethidium bromide-stained DNA. This Example compared the utility of different sample combinations of H-type and T-type Alu-, MIR- and SVA-based ITE-PCR primers for analyzing white blood cell DNA using the AlmivaScan sequencing platform in terms of the gel-electrophoresis properties of the amplicons produced by them. The sequences of the primers are provided in Table 2 below.

Figure 10:
FIG. 10 shows gel electrophoretograms of amplicons obtained by ITE-PCR in the presence of 12.5 ng of human white blood cell DNA using different sets of ITE-PCR primers. Lane A is an electrophoretogram of DNA molecular weight (M.W.) markers. Lanes B-P show gel electrophoretograms of ITE-PCR amplicons obtained using various combinations of ITE-PCR primers as listed in Table 1 below, the sequences of which are described in Example 7.

As shown in FIG. 10, the gel electrophoretograms obtained using different primer combinations varied in their intensity of DNA staining and the extent to which the gel

TABLE 2

| Four-Alu Primer set comprising: | | SEQ ID NO: |
|---|---|---|
| AluY66H21 | 5'-TGGTCTCGATCTCCTGACCTC-3' (H-type) | 2 |
| AluY278T18 | 5'-GAGCGAGACTCCGTCTCA-3' (T-Type) | 3 |
| L12A/8 | 5'-TGAGCCACCGCG-3' (H-Type) | 4 |
| R12A/267 | 5'-AGCGAGACTCCG-3' (T-Type) | 5 |
| Other Alu-consensus primers: | | |
| AluYa5/a8 | 5'-AGCTTGCAGTGAGCTGAGAT-3' (T-Type) | 6 |
| AluYb8/b9 | 5'-GTCCGCAGTCCGGCCTGGGC-3' (T-Type) | 7 |
| AluYk4/k12 | 5'-GATAGCGCCACTGCAGTCC-3' (T-Type) | 8 |
| MIR-consensus primers: | | |
| MIR17, | 5'-AGTGACTTGCTCAAGGT-3' (H-Type) | 9 |
| MIL17, | 5'-GCCTCAGTTTCCTCATC-3' (T-Type) | 10 |
| SVA-consensus primers: | | |
| SVAh | 5'-AGCCGAGATGGCAGCAGTA-3' (H-Type) | 11 |
| SVAt | 5'-ACCAGAGACCTTTGTTCACT-3' (T-Type) | 12 |

The primers AluY66H21 and AluY278T18 were previously reported by our group (Mei et al 2011). The primer L12A/8 was previously reported by Zietkiewicz et al (1992). The primer R12A/267 was previously reported by Srivastava et al (2005). The primers MIR17 and MIL17 were previously reported by Jurka et al (1995). The primers AluYa5/a8, AluYb8/b9, AluYk4/k12, SVAh and SVAt have been designed for usage in the present invention based on the known sequences of AluY subfamilies found in FIG. 6 to be enriched in the neighborhoods of midCNVGs, and known sequences of SVAs respectively (Hubly et al 2016).

Using the various primers listed above in Table 2, ITE-PCR was performed as follows: 15 ml of whole blood was mixed gently with 30 ml of red blood cell lysis buffer containing 8.26g ammonium chloride, 1.0 g potassium bicarbonate, 37 mg EDTA and incubated for 30 min at 4° C. Cell nuclei were isolated by centrifugation for 30 min at 3500 rpm at 4° C. These red blood cell lysis and centrifugation steps were repeated until the sedimented cell nuclei pellet was yellowish white in color. DNA was prepared from the pellet by means of phenol-chloroform extraction. ITE-PCR amplification was performed using a PCR reaction mixture containing a defined selection of PCR primers. Each mixture contained in 25-µl: 2 µl BIOLINE 10×NH$_4$ buffer (160 mM ammonium sulfate, 670 mM Tris-HCl, pH 8.8, 0.1% stabilizer; www.bioline.com), 3 mM MgCl$_2$, 0.15 mM dNTP mix, 1 unit Taq polymerase, 12.5 ng white blood cell DNA sample, and a combination of ITE-PCR primers at 0.050 µM each. For each reaction mixture, DNA denaturation was carried out at 95° C. for 5 min, followed by 30 cycles each of 30 s at 95° C., 30 s at 50° C., and 5 min at 72° C., and finally another 7 min at 72° C. An 8-pl aliquot of the reaction mixture mixed with 2-µl loading dye was subjected to agarose gel electrophoresis, ethidium bromide staining and UV visualization.

yielded a smeared or banded pattern. The amplicons in Lanes C, E and G displayed a distinctly banded pattern of ethidium bromide-stained DNA, and Lanes B, I, K and M yielded a relatively weakly-stained gel. Since only MIR-based primers were employed in Lanes C and E, only SVA-based primers were employed in Lane G, and less than five Alu-based primers were employed in Lanes B, I, K and M, these results suggest that use of only MIR-based primers, only SVA-based primers, or inadequate Alu-based primers generated amplicons of lesser quality. Lanes D and H, using four Alu-based primers with supplementation by one MIR-based or two SVA-based primers, produced a smeared pattern and useful staining. Lanes J, L and N, each employing five Alu-based primers, gave a smeared pattern with strong staining. Notably, Lanes F, O and P, using a combination of either four Alu-based and two MIR-based primers, or seven Alu-based primers together with one or two MIR-based and two SVA-based primers, yielded a mainly smeared pattern with intense staining.

Example 8

In this Example, ITE-PCR was carried out as described in Example 7 using the same set of Lanes A-P ITE-PCR primers, except that 12.5 ng human sputum DNA sample was employed in each 25-ul ITE-PCR incubation. The gel electrophoretograms obtained (FIG. 11) were largely comparable to those in Example 7. Lanes C, E and M were distinctly banded. Lanes F and J were quite strongly stained and smeared. Lanes O and P were intensely stained and smeared.

Example 9

In this Example, ITE-PCR was carried out as described in Example 7 using the same set of Lanes A-P ITE-PCR primers, except that 125 ng human fecal DNA sample was employed in each 25-μl ITE-PCR incubation. The gel electrophoretograms obtained (FIG. 12) were also largely comparable to those in Examples 7 and 8. Lanes C, I and M were distinctly banded. Lanes J and 0 were strongly stained with some visible bands. Lanes L and P were intensely stained and smeared.

Previously, the scientific publication titled "AluScan: a method for genome-wide scanning of sequence and structure variations in the human genome" by Mei, Ding, Xue et al (2011) showed that, when using PCR primers based on Alu-consensus sequences to amplify inter-Alu sequences, amplicons up to 6 kb in length were obtained, and a smeared-gel electrophoretogram provided a reliable criterion for the successful amplification and sequencing of >10 Mb of human genomic sequences derived from 8,000 genes with the discovery of 357 loss of heterozygosities (LOHs), 274 somatic single nucleotide variations (SNVs), 341 somatic indels and 7 SNV hotspots from the comparison of a glioma/control genome pair. In Examples 7-9, the gel electrophoretograms obtained with different primer sets were largely additive in terms of the number and variety of primers employed (FIGS. 10-12), indicating that there was evident collaboration and little interference between the Alu-based, MIR-based and SVA-based primers in the ITE-PCR amplification process. The collaboration between the primers was in accord with FIG. 1, which shows that while the usage of Alu-based primers alone amplifies only inter-Alu sequences in the genome, the joint usage of Alu, MIR and SVA primers enables the amplification of inter-Alu, inter-MIR, inter-SVA, inter-Alu-MIR, inter-Alu-SVA and inter-MIR-SVA sequences, thereby vastly enhancing the scope of sequence capture. Lane P, which employed Alu-based, MIR-based and SVA-based primers, yielded intensely stained and smeared electrophoretograms with white blood cell DNA, sputum DNA as well as fecal DNA. Lanes O, F and L also yielded strongly stained and smeared electrophoretograms. These results indicate that the AlmivaScan sequencing platform is capable of generating a huge number of different of ITE sequence segments from both cellular DNA and DNA from body exudates and excretions for MPS analysis through the usage of varied combinations of ITE-PCR primers. Since the primer combinations employed in FIGS. 10-12 represented only some but not all possible combinations of Alu-, MIR- and SVA-based primers, sequence capture can be readily modulated and refocused by employment of Alu-, MIR- and SVA-based primer combinations not included in Examples 7-9. As well, AlmivaScan can be extended to cover genomic sequences in the vicinity of additional retrotransposons and repeating elements by including in the ITE-PCR reaction mixture PCR primers based on the consensus sequences of these additional retrotransposons and repeating sequences, provided that such additional retrotransposons and repeating sequences are generally absent from microbial and viral DNAs.

Microorganisms comprise up to 60% of the dry mass of human feces (Stephen and Cummings 1980). Since the phenol-chloroform DNA extraction method employed to prepare DNA from the sputum and fecal samples in Examples 8 and 9 did not incorporate any steps to exclude microbial DNA, these DNA samples can be expected to contain a variety of microbial DNA. In fact, owing to the substantial microbial DNA content of feces, while 12.5 ng white blood cell DNA or sputum DNA was sufficient sample for the ITE-PCR incubations to yield an abundance of human amplicons in Examples 7 and 8, 125 ng of fecal DNA had to be employed in the ITE-PCR incubations in Example 9. Importantly, the amplicon electrophoretograms obtained in Examples 8 and 9 were largely similar to those obtained in Example 7, which indicates that AlmivaScan analysis of human DNA is highly resistant to interference by the microbial DNA in feces even when the amount of microbial DNA in feces may be expected to far exceed that of human DNA. However, while the Alu and SVA transposable elements are present only in primate and hominid DNAs respectively, the MIR transposable elements are present in all mammalian DNAs. Therefore, in order to minimize interference from the presence of mammalian DNAs derived from pork, beef, lamb or other mammalian foodstuff in the feces, it would be important to conduct AlmivaScan analysis on human fecal samples taken following a 72-hour mammalian meat or tissue-free diet. The intensely stained and well-smeared gel electrophoretograms of ITE-PCR amplicons prepared from such fecal DNA in Lanes P and L in FIG. 12 showed the effective capture of human DNA ITE-PCR amplicons despite the large presence in the sample of microbial DNA. In the event that pre-sampling abstention from foods containing mammalian meat and tissue is not possible, it would be necessary to exclude MIR consensus sequence-based primers from the ITE-PCR primer mixtures employed for the preparation of the ITE-PCR amplicons In view of the above, it will be seen that the several objects of the invention are achieved and other advantageous results attained.

As various changes could be made in the above methods without departing from the scope of the invention, it is intended that all matter contained in the above description and shown in the accompanying drawings shall be interpreted as illustrative and not in a limiting sense.

U.S. PATENT DOCUMENTS

U.S. Pat. No. 5,773,649 Issued Jun. 30, 1998, entitled "DNA MARKERS TO DETECT CANCER CELLS EXPRESSING A MUTATOR PHENOTYPE AND METHOD OF DIAGNOSIS OF CANCER CELL" Sinnett, et al.
U.S. Pat. No. 7,537,889 Issued May 26, 2009, entitled "ASSAY FOR QUANTITATION OF HUMAN DNA USING ALU ELEMENTS" Sinha et al.
U.S. 20150225722A1 Apr. 29, 2015, entitled "METHODS FOR SELECTIVE TARGETING OF HETEROCHROMATIN FORMING NON-CODING RNA" F. Ozsolek

NON-PATENT REFERENCES

Bagshaw A T M, Horwood L I, Ferguson D M et al (2017). Microsatellite polymorphisms associated with human behavioral and psychological phenotypes including a gene-environment interaction. BMC Med Genet 18, 12. doi :101186/S12881-017-0374-y
Batzer M A, Deininger P L (2002). Alu repeats and human genomic diversity. Nat Rev Genet 2002, 3:370-379.
Claussnitzer M, Dankei S N, Kim K H et al (2015). *FTO* obesity variant circuitry and adipose browning in humans. New Engl J Med 373, 895-907.
Ding, X., Tsang, SY., Xue, H et al (2014). Application of machine learning to development of copy number variation-based prediction of cancer risk. *Genomics Insights* 7, 1-11.
Forbes S A et al.(2015). COSMIC: exploring the world's knowledge of somatic mutations in human cancer. Nucleic Acids Res 43, D805-811.

Fujimoto A, Nishida N, Kimura R et al (2009). *FGFR2* is associated with hair thickness in Asian populations. J Hum Genet 54, 461-465.

Gianfrancesco O, Bubb V J, Quinn J P (2017) SVA retrotransposons as potential modulators of neuropeptide gene expression. Neuropeptides 64, 3-7 (2017).

Hubley R, Finn R D, Clements J et al. (2016). The Dfam database of repetitive DNA families. Nucleic Acids Res 44, D81-89.

Iourov L Y, Vorsanova S G, Yurov Y B (2008). Chromosomal mosaicism goes global. Mol Cytogenet 1:26. doi 10.1186/1755-8166-1-26.

Jurka J, Zietkiewicz E, Labuda D (1995). Ubiquitous mammalian-wide interspersed repeats (MIRs) are molecular fossils from the mesozoic era. Nucleic Acids Res 23, 170-175.

Kass D H, Batzer M A (1995). Inter-Alu polymerase chain reaction: advancements and applications. Anal Biochem 228, 185-193.

Kim J J, Park Y M, Baik K H et al. (2012). Exome sequencing and subsequent association studies identify five amino acid-altering variants influencing human height. Hum Genet 131, 471-478.

Krajinovic M, Richer C, Labuda D, Sinnett D (1996). Detection of a mutator phenotype in cancer cells by inter-Alu polymerase chain reaction. Cancer Res 56, 2733-2737.

Kumar Y, Yang J, Xue H et al (2015). Massive insterstitial copy-neutral loss-of-heterozygosity as evidence for cancer being a disease of the DNA-damage response. BMC Med Genet 8:42. doi 10.1186/s12920-015-0104-2.

Li X, Tan L, Liu X et al. (2010). A genome wide association study between copy number variation (CNV) and human height in Chinese population. J Genet Genomics 37, 779-785.

Lo WS, Lau CF, Xue H et al (2004). Association of SNPs and haplotypes in GABAA receptor β2 gene with schizophrenia. Mol Psychiatry 9, 603-608.

Mbarek H, Steinberg S, Nyholt et al (2016). Identification of common genetic variants influencing dizygotic twinning and female fertility. Am Hum Genet 98, 898-908.

Medland SE, Nyholt DR, Painter et al (2009). Common variants in the trichohyalin gene are associated with straight hair in Europeans. Am J Hum Genet 85, 750-755.

Mei L, Ding, X, Xue H et al. (2011). AluScan: a method for genome-wide scanning of sequence and structure variations in the human genome. BMC Genomics 12:564. doi: 10.1186/1471-2164-12-564.

Ng, S K, Hu T, Xue, H. et al (2016). Feature co-localization landscape of the human genome. Sci Rep, 6, 20650. doi:10.1038/srep20650.

Ng S K, Xue H (2006). Alu-associated enhancement of single nucleotide polymorphisms in the human genome. Gene 368, 110-116.

North B V, Curtis D, Sham P C (2002). A note on the calculation of empirical P values from Monte Carlo procedures. Am J Hum Genet 71, 439-441.

Payseur B A, Jing P, Haasl R J (2011). A genomic portrait of human microsatellite variation. Mol Biol Evol 28, 303-312.

Quinn J P, Bubb V J (2014) SVA retrotransposons as modulators of gene expression. Mobile Genet Elements 4, e32102.

Sawaya S M, Bagshaw A T, Buschiazzo E (2012). Promoter microsatellites as modulators of human gene expression. In Tandem Repeat Polymorphisms. ed. Hannan, A J. Landes pp. 41-54.

Schlien A, Malkin D (2009). Copy number variations and cancer. Genomics Med 1:62. DOI:10.1186/gm62.

Smit AFA, Hubley R, Green P. (2010) RepeatMasker Open-3.0. www.repeatmasker.org, 1996-2010.

Stephen A M, Cummings J W (1980). The microbial contribution to human fecal mass. J Med Microbiol 13, 45-56.

Srivastava T, Seth A, Datta K et al (2005). Inter-Alu PCR detects high frequency of genetic alterations in glioma cells exposed to sub-lethal cisplatin. International J. Cancer 117:683-9.

Sturm R A, Duffy D L, Zhao Z Z et al (2008). A single SNP in an evolutionary conserved region within intron 86 of the HERC2 gene determines human blue-brown eye color. Am J Hum Genet 82, 424-431.

Walker J A, Kilroy G E, Xing J et al (2003). Human DNA quantitation using Alu element-based polymerase chain reaction. Anal Biochem 315, 122-128.

Zhao C, Xu Z, Xue H et al (2009). Alternative-splicing in the exon-10 region of GABAA receptor β2 subunit gene: relationships between novel isoforms and psychotic disorders. PLoS One 4, e6977.

Zietkiewicz E, Labuda M, Sinnett D, Glorieux F H, Labuda D (1992). Linkage mapping by simultaneous screening of multiple polymorphic loci using Alu oligonucleotide-directed PCR. Proc Natl Acad Sci USA 1992, 89:8448-8451.

---

What is claimed is:

1. A method for identifying one or more genomic variations in human genomic DNA, the method comprising:
   forming an assay mixture comprising
   (a) a test sample comprising human genomic DNA;
   (b) five or more primers, wherein each primer comprises a consensus sequence based on the sequence of a transposable element (TE) or other repeating element found within the human genome, and wherein the TE or other repeating element is not typically found in microbial DNA;
   (c) free deoxynucleotide triphosphates (dNTPs) comprising adenine (A), cytosine (C), guanine (G), and thymine (T) bases;
   (d) a thermostable DNA polymerase; and
   (e) a buffer solution;
   performing a polymerase chain reaction (PCR) on the assay mixture to produce an array of amplicons comprising inter-transposable element (ITE) genomic segments;
   sequencing the amplicons using high-throughput DNA sequencing; and
   comparing sequences of the amplicons to a sequence from the same region of the human genome in a control DNA sample to identify one or more genomic variations between the test sample and the control DNA sample;
   wherein the assay mixture comprises:
   (a) at least five primers, wherein the primers comprise the nucleotide sequences of SEQ ID NOs. 2, 3, 4, 5, and 9;
   (b) at least six primers, wherein the primers comprise the nucleotide sequences of SEQ ID NOs. 2, 3, 4, 5, 11, and 12;
   (c) at least five primers, wherein the primers comprise the nucleotide sequences of SEQ ID NOs. 2, 3, 4, 5, and 8;
   (d) at least five primers, wherein the primers comprise the nucleotide sequences of SEQ ID NOs. 2, 3, 4, 5, and 7;
   (e) at least five primers, wherein the primers comprise the nucleotide sequences of SEQ ID NOs. 2, 3, 4, 5, and 6;
   (f) at least six primers, wherein the primers comprise the nucleotide sequences of SEQ ID NOs. 2, 3, 4, 5, 9, and 10;
   (g) at least ten primers, wherein the primers comprise the nucleotide sequences of SEQ ID NOs. 2, 3, 4, 5, 6, 7, 8, 9, 11, and 12; or
   (h) at least eleven primers, wherein the primers comprise the nucleotide sequences of SEQ ID NOs. 2, 3, 4, 5, 6, 7, 8, 9, 10, 11, 12.

2. The method of claim 1, wherein the one or more genomic variations comprise a single nucleotide polymorphism (SNP), a microsatellite (MST), a germline copy number variation (CNVG), a somatic copy number variation (CNVT), or a combination of any thereof.

3. The method of claim 1, wherein the test sample comprises human white blood cells, human sputum, human feces, human plasma, human serum, human urine, human saliva, or a combination of any thereof.

4. The method of claim 1, wherein the test sample comprises human feces obtained from a human subject, wherein the human subject has consumed a diet free of mammalian meat or tissue for at least about 72 hours prior to collection of the test sample.

5. The method of claim 1, wherein the test sample comprises a sub-microgram quantity of human DNA.

6. The method of claim 1, wherein the test sample further comprises microbial DNA, plant DNA, or both microbial DNA and plant DNA.

7. The method of claim 1, wherein the high-throughput DNA sequencing comprises massively parallel sequencing and the massively parallel sequencing produces a massively parallel inter-transposable element (ITE) sequence pattern.

8. The method of claim 1, wherein the method further comprises transforming data obtained from the sequencing into a computer-readable format prior to comparing the sequences of the amplicons to the sequence of the control DNA sample.

9. A method for identifying one or more genomic variants associated with a trait or a disease, the method comprising:
   forming a first assay mixture comprising
   (a) a first test sample comprising human genomic DNA, wherein the first test sample is obtained from a human subject having the trait or the disease;
   (b) five or more primers, wherein each primer comprises a consensus sequence based on the sequence of a transposable element (TE) or other repeating element found within the human genome, and wherein the TE or other repeating element is not typically found in microbial DNA;
   (c) free deoxynucleotide triphosphates (dNTPs) comprising adenine (A), cytosine (C), guanine (G), and thymine (T) bases;
   (d) a thermostable DNA polymerase; and
   (e) a buffer solution;
   forming a second assay mixture comprising
   (a) a second test sample comprising human genomic DNA, wherein the second test sample is obtained from a human subject that does not have the trait or the disease;
   (b) five or more primers, wherein the sequences of the five or more primers are identical to the sequences of the five or more primers in the first assay mixture;
   (c) free deoxynucleotide triphosphates (dNTPs) comprising adenine (A), cytosine (C), guanine (G), and thymine (T) bases;
   (d) a thermostable DNA polymerase; and
   (e) a buffer solution;
   performing polymerase chain reactions (PCR) on each of the first and second assay mixtures to produce a first array of amplicons comprising inter-transposable element (ITE) genomic segments from the first test sample and a second array of amplicons comprising inter-transposable element (ITE) genomic segments from the second test sample; and
   comparing sequences of the first array of amplicons to sequences from the second array of amplicons to identify one or more genomic variations associated with the trait or the disease;
   wherein the first assay mixture and/or the second assay mixture comprise:
   (a) at least five primers, wherein the primers comprise the nucleotide sequences of SEQ ID NOs. 2, 3, 4, 5, and 9;
   (b) at least six primers, wherein the primers comprise the nucleotide sequences of SEQ ID NOs. 2, 3, 4, 5, 11, and 12;
   (c) at least five primers, wherein the primers comprise the nucleotide sequences of SEQ ID NOs. 2, 3, 4, 5, and 8;
   (d) at least five primers, wherein the primers comprise the nucleotide sequences of SEQ ID NOs. 2, 3, 4, 5, and 7;
   (e) at least five primers, wherein the primers comprise the nucleotide sequences of SEQ ID NOs. 2, 3, 4, 5, and 6;
   (f) at least six primers, wherein the primers comprise the nucleotide sequences of SEQ ID NOs. 2, 3, 4, 5, 9, and 10;
   (g) at least ten primers, wherein the primers comprise the nucleotide sequences of SEQ ID NOs. 2, 3, 4, 5, 6, 7, 8, 9, 11, and 12; or
   (h) at least eleven primers, wherein the primers comprise the nucleotide sequences of SEQ ID NOs. 2, 3, 4, 5, 6, 7, 8, 9, 10, 11, 12.

* * * * *

UNITED STATES PATENT AND TRADEMARK OFFICE
CERTIFICATE OF CORRECTION

PATENT NO. : 11,634,774 B2
APPLICATION NO. : 16/613667
DATED : April 25, 2023
INVENTOR(S) : Hong Xue It is certified that error appears in the above-identified patent and that said Letters Patent is hereby corrected as shown below:

In the Claims

Column 34, Claim 9, Line 21: "and/or" should read -- and --.

Signed and Sealed this
Thirtieth Day of April, 2024

Katherine Kelly Vidal
*Director of the United States Patent and Trademark Office*

SEQUENCE LISTING

```
<160> NUMBER OF SEQ ID NOS: 12

<210> SEQ ID NO 1
<211> LENGTH: 14
<212> TYPE: DNA
<213> ORGANISM: Artificial sequence
<220> FEATURE:
<223> OTHER INFORMATION: Consensus sequence

<400> SEQUENCE: 1
aaaaatacaa aaaa                                                       14

<210> SEQ ID NO 2
<211> LENGTH: 21
<212> TYPE: DNA
<213> ORGANISM: Artificial sequence
<220> FEATURE:
```

```
<223> OTHER INFORMATION: Primer

<400> SEQUENCE: 2
tggtctcgat ctcctgacct c                                              21

<210> SEQ ID NO 3
<211> LENGTH: 18
<212> TYPE: DNA
<213> ORGANISM: Artificial sequence
<220> FEATURE:
<223> OTHER INFORMATION: Primer

<400> SEQUENCE: 3
gagcgagact ccgtctca                                                  18

<210> SEQ ID NO 4
<211> LENGTH: 12
<212> TYPE: DNA
<213> ORGANISM: Artificial sequence
<220> FEATURE:
<223> OTHER INFORMATION: Primer

<400> SEQUENCE: 4
tgagccaccg cg                                                        12

<210> SEQ ID NO 5
<211> LENGTH: 12
<212> TYPE: DNA
<213> ORGANISM: Artificial sequence
<220> FEATURE:
<223> OTHER INFORMATION: Primer

<400> SEQUENCE: 5
agcgagactc cg                                                        12

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
agcttgcagt gagctgagat                                                20

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
gtccgcagtc cggcctgggc                                                20

<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8
gatagcgcca ctgcagtcc                                                 19
```

```
<210> SEQ ID NO 9
<211> LENGTH: 17
<212> TYPE: DNA
<213> ORGANISM: Artificial sequence
<220> FEATURE:
<223> OTHER INFORMATION: Primer

<400> SEQUENCE: 9
agtgacttgc tcaaggt                                              17

<210> SEQ ID NO 10
<211> LENGTH: 17
<212> TYPE: DNA
<213> ORGANISM: Artificial sequence
<220> FEATURE:
<223> OTHER INFORMATION: Primer

<400> SEQUENCE: 10
gcctcagttt cctcatc                                              17

<210> SEQ ID NO 11
<211> LENGTH: 19
<212> TYPE: DNA
<213> ORGANISM: Artificial sequence
<220> FEATURE:
<223> OTHER INFORMATION: Primer

<400> SEQUENCE: 11
agccgagatg gcagcagta                                            19

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
accagagacc tttgttcact                                           20
```